US012656458B2

(12) United States Patent (10) Patent No.: US 12,656,458 B2
Fishler et al. (45) Date of Patent: Jun. 16, 2026

(54) RADAR BASED RANGE DETERMINATION AND VALIDATION

(71) Applicant: Neteera Technologies Ltd, Jerusalem (IL)

(72) Inventors: Ehud Fishler, Shoham (IL); Dean Ranmar, Gedera (IL)

(73) Assignee: Neteera Technologies Ltd, Jerusalem (IL)

( * ) Notice: Subject to any disclaimer, the term of this patent is extended or adjusted under 35 U.S.C. 154(b) by 259 days.

(21) Appl. No.: 18/574,349

(22) PCT Filed: Jun. 26, 2022

(86) PCT No.: PCT/IL2022/050685
§ 371 (c)(1),
(2) Date: Dec. 27, 2023

(87) PCT Pub. No.: WO2023/275865
PCT Pub. Date: Jan. 5, 2023

(65) Prior Publication Data
US 2024/0302495 A1 Sep. 12, 2024

Related U.S. Application Data

(60) Provisional application No. 63/215,998, filed on Jun. 29, 2021.

(51) Int. Cl.
G01S 7/41 (2006.01)
A61B 5/00 (2006.01)
(Continued)

(52) U.S. Cl.
CPC .............. G01S 7/415 (2013.01); A61B 5/05 (2013.01); A61B 5/7257 (2013.01); G01S 13/34 (2013.01)

(58) Field of Classification Search
CPC . G01S 7/415; G01S 13/34; A61B 5/05; A61B 5/7257
(Continued)

(56) References Cited

U.S. PATENT DOCUMENTS 4,641,137 A * 2/1987 Opitz ...................... G01S 7/415
342/52
5,087,918 A * 2/1992 May ...................... G01S 13/931
342/70
(Continued)

FOREIGN PATENT DOCUMENTS

CN       111142102 A      5/2020
EP           3492945 A1 *  6/2019  ........... G01S 5/0218
(Continued)

OTHER PUBLICATIONS

International Preliminary Report on Patentability dated Dec. 14, 2023 with Written Opinion for PCT/IL2022/050685.
(Continued)

*Primary Examiner* — Nuzhat Pervin
(74) *Attorney, Agent, or Firm* — Fleit Intellectual Property Law; Paul D. Bianco

(57) ABSTRACT

Radar-based range determination and validation. A reflected FMCW radar signal is received from a subject and sampled to generate sample vectors including signal samples for each frame of reflected radar signal. An FFT is applied to sample vectors to generate a range-time map (RTM) data matrix. An initial range estimate of subject is determined by: calculating a range score signal (RSS) by either: cross-multiplying a mean power per RTM range bin with a corresponding variance per range bin, or dividing variance per range bin with a zero-crossing per range bin to second exponent; identifying a maximum value index range bin having a maximum RSS value; and multiplying identified maximum value index range bin with a range bin spacing of range (Continued)

spectrum RSS. At least one physiological parameter is detected to verify that subject is a living entity. Range estimate is validated by determining if predetermined number of validity criteria met.

13 Claims, 17 Drawing Sheets

(51) Int. Cl.
*A61B 5/05* (2021.01)
*G01S 13/34* (2006.01)

(58) Field of Classification Search
USPC ........................................................ 342/196
See application file for complete search history.

(56) References Cited

U.S. PATENT DOCUMENTS

| | | | | | |
|---|---|---|---|---|---|
| 5,563,602 | A * | 10/1996 | Stove | G01S 13/24 | 342/96 |
| 7,046,190 | B2 * | 5/2006 | Steudel | G01S 13/584 | 342/107 |
| 8,344,942 | B2 * | 1/2013 | Jin | G01S 13/904 | 367/99 |
| 9,568,601 | B1 * | 2/2017 | Xu | G01S 13/584 | |
| 9,662,088 | B2 * | 5/2017 | Pelissier | A61B 8/543 | |
| 10,401,479 | B2 * | 9/2019 | Mabrouk | G01S 13/52 | |
| 10,436,888 | B2 * | 10/2019 | Li | G01S 13/886 | |
| 10,497,381 | B2 * | 12/2019 | Short | G10L 21/0272 | |
| 11,166,637 | B2 * | 11/2021 | Siedenburg | A61B 5/02125 | |
| 11,408,978 | B2 * | 8/2022 | Wang | A61B 5/0816 | |
| 11,653,848 | B2 * | 5/2023 | Lane | A61B 5/024 | 600/407 |
| 11,883,142 | B2 * | 1/2024 | Shay | A61B 5/681 | |
| 11,885,905 | B2 * | 1/2024 | Iwasa | G01S 7/2921 | |
| 12,274,527 | B2 * | 4/2025 | Bliss | A61B 5/7257 | |
| 2006/0071847 | A1 * | 4/2006 | Fiore | G01S 13/44 | 342/107 |
| 2015/0287422 | A1 * | 10/2015 | Short | G01S 3/74 | 704/211 |
| 2015/0323660 | A1 * | 11/2015 | Hampikian | G01S 13/347 | 342/109 |
| 2017/0074979 | A1 * | 3/2017 | Nielsen | G01S 13/38 | |
| 2018/0156911 | A1 * | 6/2018 | Pokrass | G01S 13/931 | |
| 2018/0252803 | A1 * | 9/2018 | Bilik | G01S 13/70 | |
| 2019/0086534 | A1 * | 3/2019 | Frick | G01S 13/582 | |
| 2020/0058316 | A1 * | 2/2020 | Short | H04R 3/00 | |
| 2020/0116850 | A1 * | 4/2020 | Santra | A61B 5/0507 | |
| 2020/0300972 | A1 * | 9/2020 | Wang | A61B 5/0002 | |
| 2021/0173045 | A1 * | 6/2021 | Hu | G01S 7/415 | |
| 2021/0405150 | A1 * | 12/2021 | Roh | G01S 13/536 | |
| 2022/0011423 | A1 * | 1/2022 | Li | G01S 7/023 | |
| 2022/0187436 | A1 * | 6/2022 | Alsharif | G01S 11/14 | |
| 2023/0309846 | A1 * | 10/2023 | Hyde | A61B 5/6801 | 600/407 |
| 2024/0388920 | A1 * | 11/2024 | Montalvo | H04W 16/10 | |
| 2024/0388921 | A1 * | 11/2024 | Montalvo | H04W 16/10 | |
| 2024/0388937 | A1 * | 11/2024 | Murias | H04B 17/23 | |
| 2024/0430690 | A1 * | 12/2024 | Montalvo | G06F 30/27 | |
| 2025/0150841 | A1 * | 5/2025 | Murias | H04W 24/10 | |

FOREIGN PATENT DOCUMENTS

| | | | | |
|---|---|---|---|---|
| WO | 2018/167777 | A1 | 9/2018 | |
| WO | 2020/012455 | A1 | 1/2020 | |
| WO | WO-2021028483 | A1 * | 2/2021 | G01S 13/931 |

OTHER PUBLICATIONS

International Search Report dated Nov. 6, 2022 with Written Opinion for PCT/IL2022/050685.

* cited by examiner

OBTAINING RADAR REFLECTION SIGNAL SAMPLES FROM A SUBJECT

130

PRE-PROCESSING SIGNAL TO GENERATE A RANGE-TIME MAP (RTM) MATRIX

140

DETECTING PHYSIOLOGICAL PARAMETERS OF SUBJECT

150

RANGE ESTIMATION

160

VALIDATING RANGE ESTIMATE

170

NEGATIVE VALIDATION

POSITIVE VALIDATION

ESTABLISHING RANGE OF SUBJECT BASED ON VALIDATED ESTIMATE

180

RADAR BASED RANGE DETERMINATION AND VALIDATION

FIELD OF THE INVENTION

The present invention generally relates to the fields of range estimation, temporal signal processing, and vital signs detection.

BACKGROUND OF THE INVENTION

Vital signs refer to physiological indicators of life-sustaining functions of a human body. These indicators may be measured and monitored in order to provide a health assessment of the body. Examples of vital signs include: body temperature (BT), blood pressure (BP), heart rate (HR) and respiratory rate (RR). Such parameters may be measured using standard commonly used medical devices or equipment, such as a thermometer, a blood pressure monitor, an electrocardiogram (ECG) machine, or a stethoscope. In some cases, it is beneficial to obtain vital signs measurements without requiring measurement equipment components being in direct physical contact, or even in the same vicinity, as the measured person. Certain vital sign information can be obtained remotely, such as by detecting an optical, acoustic, thermal and/or electromagnetic signal reflected from one or more body parts, followed by spatial and/or temporal processing of the reflected signal.

There are many types of distance or range sensors known in the art for measuring the distance relative to a remotely located target or object. Such sensors generally operate by transmitting a type of signal (e.g., optical, acoustic, thermal, electromagnetic) and then detecting changes in the reflected signal received from the target. For example, an ultrasonic or sonar sensor emits high-frequency ultrasonic waves, a laser rangefinder utilizes time-of-flight of emitted laser pulses, while a radar sensor can determine distance (and speed) of an object based on changes in the frequency or phase of the reflected radar signal caused by the Doppler effect. Certain distance sensors, known as proximity sensors, operate in limited ranges and can only detect the presence of nearby objects (e.g., touch screen detection in smartphones or other mobile devices). Distance measurements are used in countless applications, of which some examples include: surveillance and reconnaissance, three-dimensional modeling, meteorological monitoring, flight control systems and self-driving vehicles. Some applications may require discriminating range measurements between different types or categories of targets, such as differentiating living persons from non-human entities.

SUMMARY OF THE INVENTION

In accordance with one aspect of the present invention, there is thus provided a method for determining the range of a subject. The method includes the procedures of receiving a frequency-modulated continuous-wave (FMCW) radar signal reflected from at least one subject, and sampling the received reflected radar signal to generate a plurality of sample vectors over a selected duration, each sample vector comprising a plurality of signal samples for each frame of the reflected radar signal. The method further includes the procedure of applying a fast Fourier transform (FFT) to a plurality of sample vectors over a selected duration to generate a range-time map (RTM) data matrix. The method further includes the procedure of determining an initial range estimate of the subject by: (i) calculating a range score signal (RSS) using one of the following equations: a) cross-multiplying a mean power per range bin of the RTM with a corresponding variance per range bin (RSS=Mean Power×rng_var); and b) dividing the variance per range bin of the RTM with a zero-crossing per range bin to the second exponent $$\left(RSS = \frac{rng\_var}{ZC^2}\right);$$

(ii) identifying a maximum value index range bin having a maximum RSS value; and (iii) calculating a range estimate by multiplying the identified maximum value index range bin with a range bin spacing of the range spectrum RSS. The method further includes the procedure of detecting at least one physiological parameter of the subject to verify that the subject is a living entity. The method may further include the procedure of validating the determined range estimate by: determining if the range estimate meets a first validity criterion based on a max/min dynamic ratio (mxmn); determining if the range estimate meets a second validity criterion based on an inter-quartile range (IQR) outlier metric; determining if the range estimate meets a third validity criterion based on a modified z-score; and determining if the range estimate meets a fourth validity criterion based on the number of signal peaks of the standardized z-score. The method further includes the procedure of establishing a final range of the subject according to the range estimate if the range estimate is determined to meet at least a predetermined number of the validity criteria. The determined range estimate may be replaced with a default range value if at least one auxiliary criterion is met, where the auxiliary criterion includes: when the subject is positioned in a non-standing posture and the reflected radar signal is received from back of the subject; and/or when the determined range estimate is below a predefined minimum threshold range.

In accordance with another aspect of the present invention, there is thus provided a system for determining the range of a subject. The system includes a radar detector, configured to receive a frequency-modulated continuous-wave (FMCW) radar signal reflected from at least one subject, and to sample the received reflected radar signal to generate a plurality of sample vectors over a selected duration, each sample vector comprising a plurality of signal samples for each frame of the reflected radar signal. The system further includes a processor, configured to apply a fast Fourier transform (FFT) to a plurality of sample vectors over a selected duration to generate a range-time map (RTM) data matrix. The processor is further configured to determine an initial range estimate of the subject by: calculating a range score signal (RSS) using one of the following equations: a) cross-multiplying a mean power per range bin of the RTM and the corresponding variance per range bin (RSS=Mean Power×rng_var); and b) dividing the variance per range bin of the RTM with a zero-crossing per range bin to the second exponent $$\left(RSS = \frac{rng\_var}{ZC^2}\right);$$

identifying a maximum value index range bin having a maximum RSS value; and calculating a range estimate by multiplying the identified maximum value index range bin with a range bin spacing of the range spectrum RSS. The processor is further configured to detect at least one physiological parameter of the subject to verify that the subject is a living entity. The processor may further be configured to validate the determined range estimate by: determining if the range estimate meets a first validity criterion based on a max/min dynamic ratio (mxmn); determining if the range estimate meets a second validity criterion based on an inter-quartile range (IQR) outlier metric; determining if the range estimate meets a third validity criterion based on a modified z-score; and determining if the range estimate meets a fourth validity criterion based on the number of signal peaks of the modified z-score. The processor is further configured to establish a final range of the subject according to the range estimate if the range estimate is determined to meet at least a predetermined number of the validity criteria. The determined range estimate may be replaced with a default range value if at least one auxiliary criterion is met, where the auxiliary criterion includes: when the subject is positioned in a non-standing posture and the reflected radar signal is received from back of the subject; and/or when the determined range estimate is below a predefined minimum threshold range.

BRIEF DESCRIPTION OF THE DRAWINGS

The present invention will be understood and appreciated more fully from the following detailed description taken in conjunction with the drawings in which.

DETAILED DESCRIPTION OF THE EMBODIMENTS

The present invention overcomes the disadvantages of the prior art by providing a method and system for determining the range or distance to a living subject, using bit-frequency detection in combination with vital signs detection to obtain an initial range estimate, and applying validation metrics to validate the range estimate with a high degree of reliability.

The terms "user" and "operator" are used interchangeably herein to refer to any individual person or group of persons using or operating the method or system of the present invention, such as a person who is determining a range measurement.

The terms "subject" and "living subject" are used interchangeably herein to refer to an individual person or group of persons upon which the method or system of the present invention is operated upon, such as a person whose range is being measured. The subject may be any living person, human or animal, characterized with vital signs reflecting the physiological functioning of its body.

The term "physiological parameter" as used herein refers to any physiological indicator, vital sign, cardiac or pulmonary metric, medical condition, or health characteristic. Examples of physiological parameters may include: heart rate, (HR), respiratory rate, (RR), heart rate variability, (HRV), respiration amplitude, (RA), respiration amplitude variability, respiration rate variability, (RRV), ballistocardiogram (BCG) signal, BCG amplitude variability, pulse wave velocity, (PWV), blood pressure (i.e. MAP, systolic and diastolic), vascular resistance, body temperature, pulse pressure variability, stroke volume and variability, body fluid (such as sweat, saliva and/or tears), body movement derived from vocal cord vibration, eye movement, body or skin movement due to speech, motion classification such as speaking or singing, change in voice sound, micro skin motions and body motion (such as seizures, tremors, shaking, trembling and/or vibrating).

The term "repeatedly" as used herein should be broadly construed to include any one or more of: "continuously", "periodic repetition" and "non-periodic repetition", where periodic repetition is characterized by constant length intervals between repetitions and non-periodic repetition is characterized by variable length intervals between repetitions.

Figure 1:
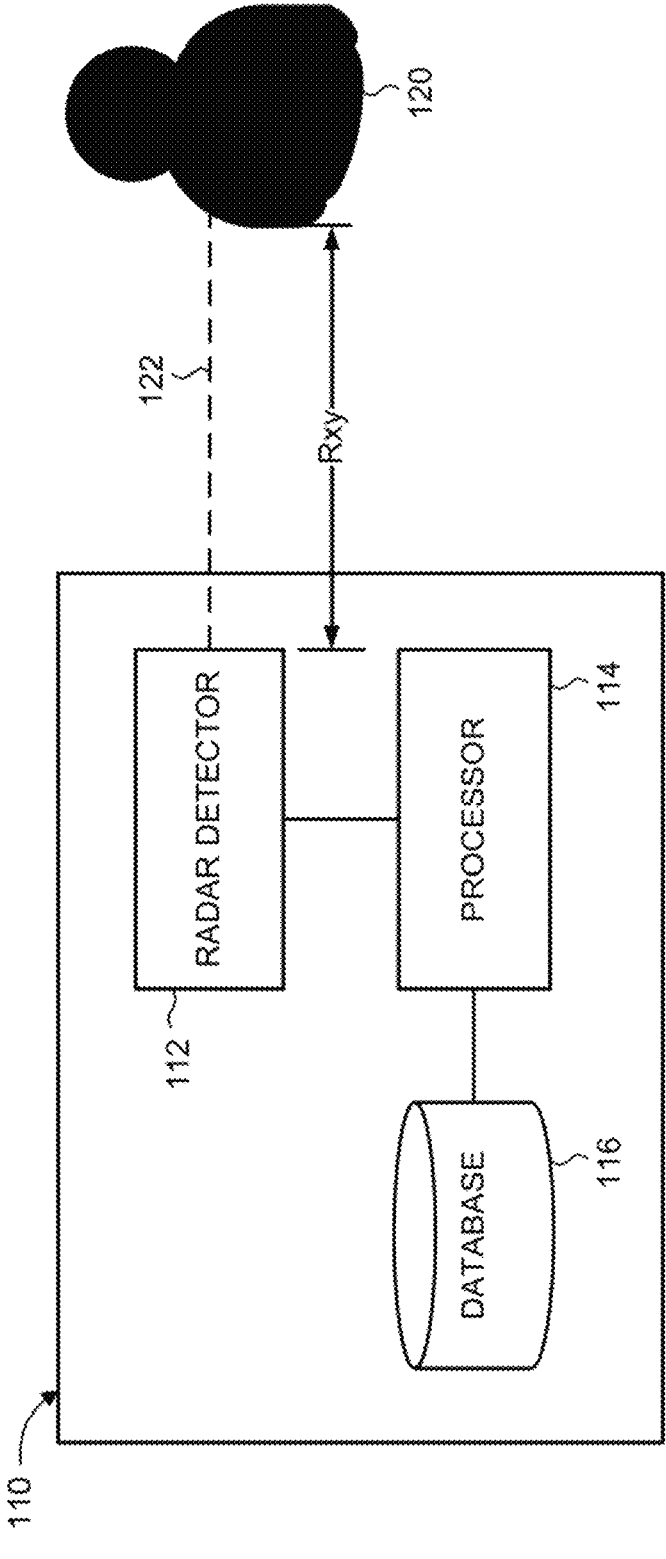
FIG. 1 is a schematic illustration of a system for determining the range from a living subject, constructed and operative in accordance with an embodiment of the present invention.

Reference is now made to FIG. 1, which is a schematic illustration of a system, generally referenced 110, for determining the range to a living subject, referenced 120, constructed and operative in accordance with an embodiment of the present invention. System 110 includes a radar detector 112, a processor 114, and a database 116. Processor 114 is communicatively coupled with radar detector 112 and with database 116.

Radar detector 112 is configured to transmit and receive a reflected radar signal 122 from subject 120. Accordingly, radar detector 112 may include at least a radar transmitter component for transmitting a radar signal, and a radar receiver component for receiving a reflected radar signal. The transmitted/received radar signal may be in the THz or sub-THz frequency band, corresponding to millimeter-wave or sub-millimeter wave radiation, such as between 0.003-1 THz, or between 50 GHZ-1 THz. The transmitted/reflected radar signal is a continuous-wave (CW) radar signal, and particularly a frequency-modulated continuous-wave (FMCW) signal. Radar detector 112 may be embodied by a THz based radar system as described for example in PCT application publication WO2018/167777A1 to Neteera Technologies, entitled "Method and device for non-contact sensing of vital signs and diagnostic signals by electromagnetic waves in the sub terahertz band", and PCT application publication WO2020/012455A1 to Neteera Technologies, entitled "A sub-THz and THz system for physiological parameters detection and method thereof".

Processor 114 receives information or instructions from other components of system 110 and performs required data processing. In particular, processor 114 receives and processes a reflected radar signal 122 obtained by radar detector to extract a range estimate, as will be elaborated upon further hereinbelow. Database 116 stores information relating to the operation of system 110. Database 116 may be represented by one or more local servers or by remote and/or distributed servers, such as in a cloud storage platform.

Information may be conveyed between the components of system 110 over any suitable data communication channel or network, using any type of channel or network model and any data transmission protocol (e.g., wired, wireless, radio, WiFi, Bluetooth, and the like). For example, system 110 may store, manage and/or process data using a cloud computing model, and the components of system 110 may communicate with one another and be remotely monitored or controlled over the Internet, such as via an Internet of Things (IoT) network. The components and devices of system 110 may be based in hardware, software, or combinations thereof. It is appreciated that the functionality associated with each of the devices or components of system 110 may be distributed among multiple devices or components, which may reside at a single location or at multiple locations. For example, the functionality associated with processor 114 may be distributed between a single processing unit or multiple processing units. Processor 114 may be part of a server or a remote computer system accessible over a communications medium or network, such as a cloud computing platform. Processor 114 may also be integrated with other components of system 110, such as incorporated with radar detector 112.

System 110 may optionally include and/or be associated with additional components not shown in FIG. 1, for enabling the implementation of the disclosed subject matter. For example, system 110 may include a user interface (not shown) for allowing a user to control various parameters or settings associated with the components of system 110, and a display device (not shown) for visually displaying information relating to the operation of system 110.

Figure 2:
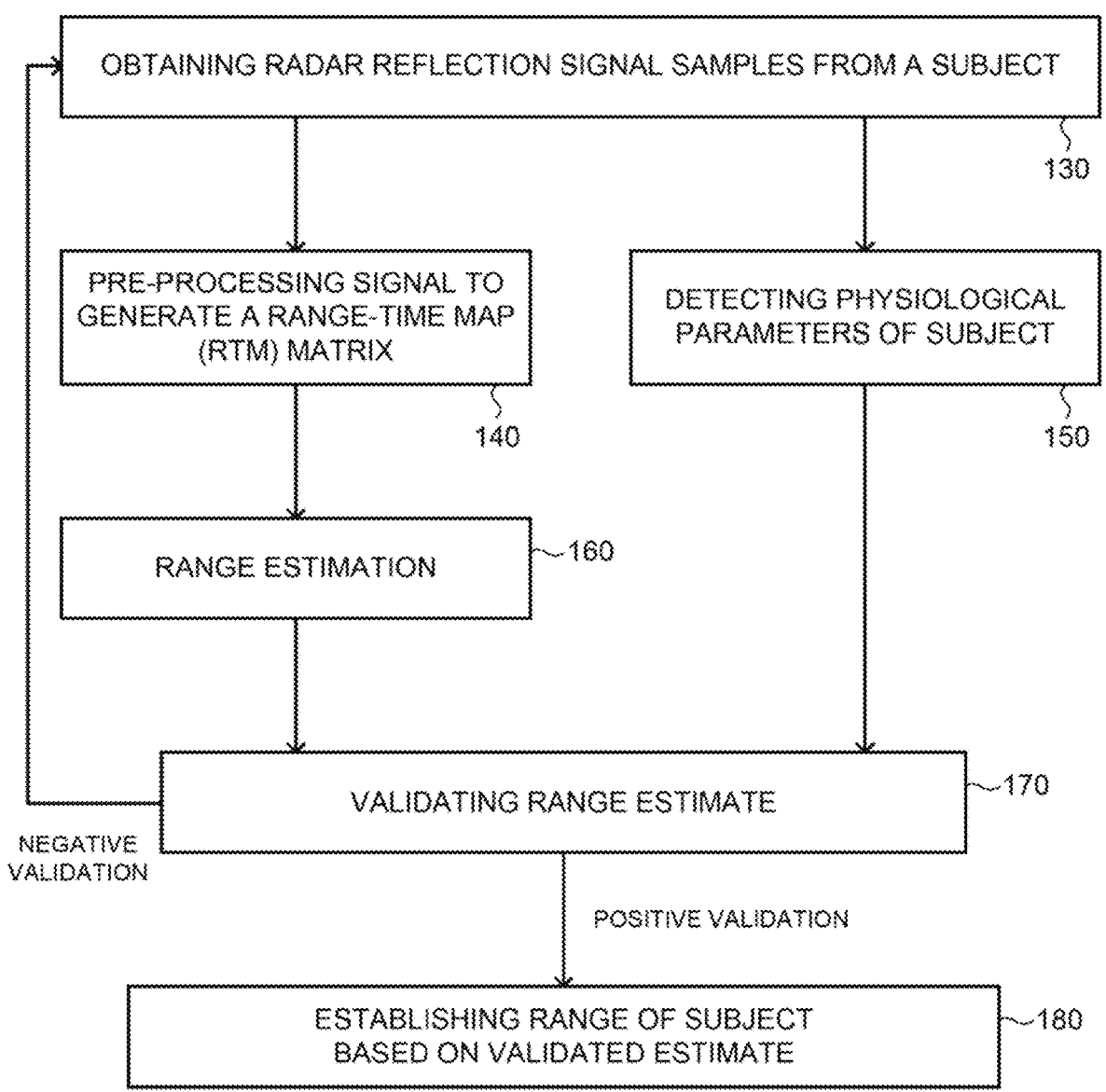
FIG. 2 is a block diagram of a method for determining the range from a living subject, operative in accordance with an embodiment of the present invention.
Figure 3:
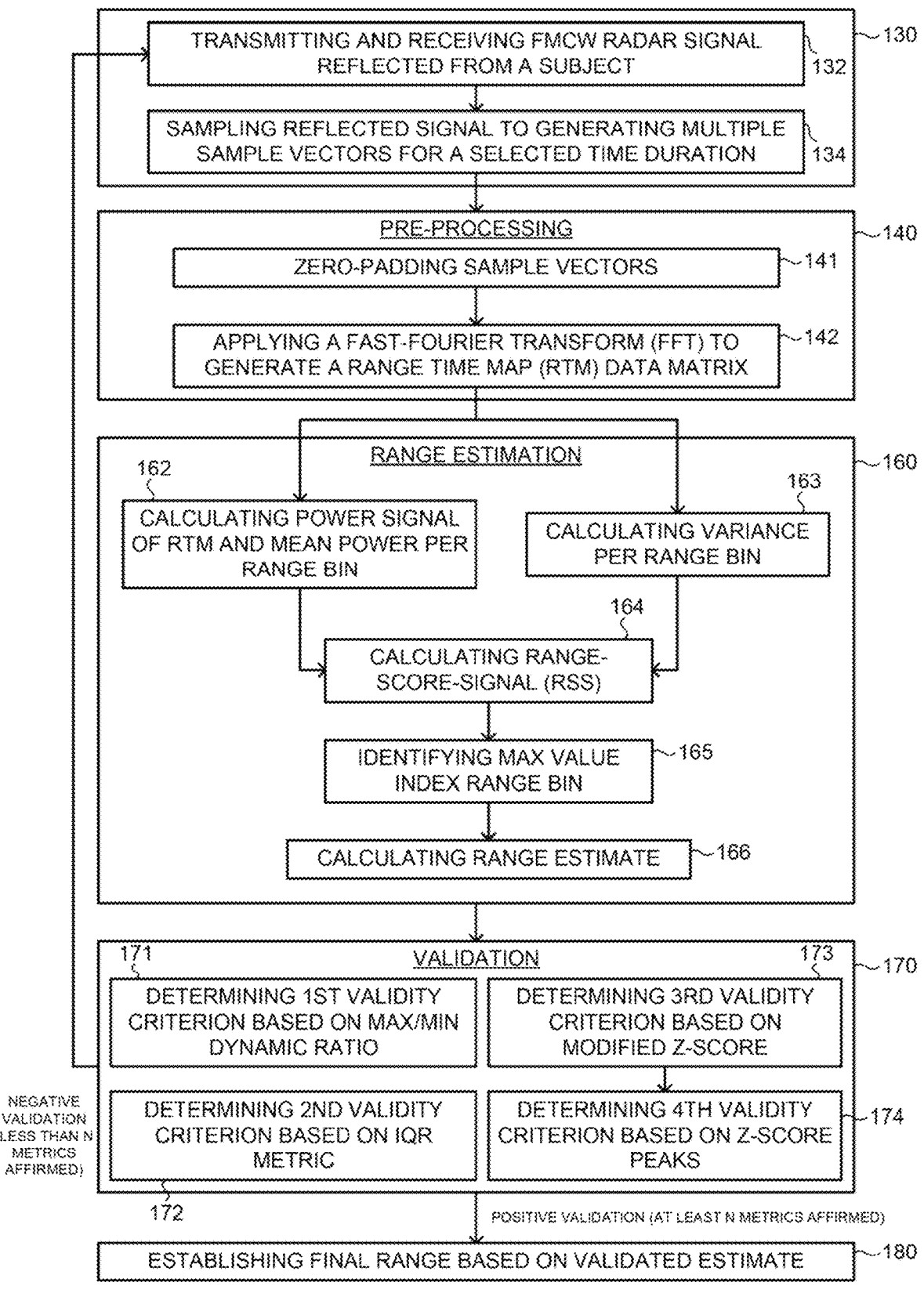
FIG. 3 is an expanded block diagram of the method of FIG. 2, operative in accordance with an embodiment of the present invention.

Reference is now made to FIGS. 2 and 3. FIG. 2 is a block diagram of a method for determining the range from a living subject, operative in accordance with an embodiment of the present invention, and FIG. 3 is an expanded block diagram of the method of FIG. 2.

Radar reflection signal samples are obtained from a subject in an initial stage 130 that includes procedures 132 and 134. In procedure 132, a radar signal is transmitted toward a subject and a reflected radar signal is received from the subject. Referring to FIG. 1, radar detector 112 transmits a radar signal and receives reflected radar signal 122 reflected back from subject 120. Radar signal 122 may be an FMCW signal in the bandwidth range between 50 GHz and 1 THz. In procedure 134, the received radar signal is sampled to generate multiple sample vectors for a selected time duration. Referring to FIG. 1, radar detector 112 samples reflected radar signal 122 to generate a selected number (N) of samples for each frame or "chirp" (i.e., received radar pulse) over a selected time duration (e.g., 6 seconds). In particular, each chirp/frame is sampled to generate a vector of samples per chirp/frame. The sampled signal vector is the intermediate frequency (IF) from the combining of the transmitted (Tx) and received (Rx) signals. The frames may be sampled at a relatively high frequency rate, such as 1 MHz.

The sample vectors then undergo a pre-processing stage 140 that includes procedures 141 and 142. In an optional procedure 141, each sample vector is extended using zero-padding. Referring to FIG. 1, processor 114 applies a zero-padding process to each sample vector per frame/chirp of received radar signal 122, by inserting zero-value bits or samples to the end of the respective vector to generate a corresponding vector having an extended bit (or sample) length, so as to increase the accuracy of the subsequent range estimate. The zero-padding may be determined in accordance with the desired range accuracy. For example, a frame vector having 128 samples may be zero-padded by appending 128 null (zero) value samples to produce a corresponding 256 sample-length frame vector. In procedure 142, a fast Fourier transform (FFT) is applied to generate a range-time map (RTM) data matrix. Referring to FIG. 1, processor 114 applies an FFT to the zero-padded sample vector (e.g., 256 samples) for each frame/chirp over a selected duration to generate a plurality of range bins represented as a "range-time map (RTM)" data matrix. The RTM matrix corresponds to a number of frames over a selected duration (e.g., 5000 frames over 6 seconds), where the collection of sample vectors for those frames and time span is assembled to generate the RTM after each vector is transformed from time domain to frequency domain via FFT. Accordingly, the FFT is characterized by a fast-sampling frequency for the sample rate (i.e., rate at which samples per frame is obtained) and by a slow-sampling frequency for the frame rate (i.e., the rate at which frames are obtained, or number of frames per second).

The RTM undergoes further processing in a "range estimation" stage 160, which includes procedures 162, 163, 164, 165, 166. The range estimation stage is intended to extract the most prominent range and range bin signal from the RTM. The range is estimated using a "Range Score Signal (RSS)" metric, which may be derived using two alternative methodologies.

A first methodology combines two metrics: the subject range via a corresponding "bit-frequency" detection, and the displacement variance per range bin via the magnitude change corresponding to the combined movements of the subject (vital signs combined with body movements), which are cross-multiplied to produce an RSS. Accordingly, in procedure 162A, a power signal of the RTM and a mean power per range bin of the RTM is calculated. Referring to FIG. 1, processor 114 determines a power signal function of the RTM, such as by using the following equation:

$$\text{rng\_gates} = \text{abs}(\text{data\_matrix})^2 \qquad \text{(Eq. 1)}$$

where "data_matrix" represents the RTM.

Processor 114 further determines a mean power signal function of the RTM, such as by using the following equation:

$$\text{Mean Power} = 10 * \log_{10}(\text{rng\_gates}) \qquad \text{(Eq. 2)}$$

or equivalently: Mean Power=log(rng_gates)

where "rng_gates" represents power (as calculated in Eq.1).

Processor 114 calculates a range bin variance of the RTM (in procedure 163) by estimating the bin variance across the slow sampling frequency of the RTM, such as by using the following equation:

$$rng\_var = var(data\_matrix) \qquad \text{(Eq. 3)}$$

Processor 114 determines a range score signal (RSS) of the RTM (in procedure 164), by applying a cross multiplication (element by element) of the log-transformed range bin power (Mean power as calculated in Eq.2) and the corresponding range bin variance (as calculated in Eq.3):

$$RSS = \text{Mean Power} \times rng\_var \qquad \text{(Eq. 4)}$$

A second methodology for deriving the RSS utilizes a zero-crossing (ZC) for each range bin combined with the range bin variance. Accordingly, in procedure 162B, a zero-crossing is calculated for each range bin. Referring to FIG. 1, processor 114 determines a bin offset using the following equation:

$$bin\_offset\_reduced = bin\_data - mean(bin\_data) \qquad \text{(Eq. 5)}$$

The bin zero-crossing (ZC) is then calculated by the number of times the sign (positive or negative) of the signal changes. The ZC is clipped by a minimum value.

Processor 114 then calculates a range bin variance of the RTM (in procedure 163) by estimating the bin variance across the slow sampling frequency of the RTM using Eq.3. Processor 114 further determines a range score signal (RSS) of the RTM (in procedure 164) by dividing the variance per range bin of the RTM with a zero-crossing per range bin to the second exponent using the following equation:

$$\left(RSS = \frac{rng\_var}{ZC^2}\right) \qquad \text{(Eq. 6)}$$

Regardless of how the RSS is derived, only a range bin having the most prominent RSS signal is established as a "valid candidate" target range.

In procedure 165, a maximum value index range bin is identified. Referring to FIG. 1, processor 114 identifies the range bin characterized as the index of the max value using the following equation:

$$rng\_bin = arg\_max(RSS) \qquad \text{(Eq. 7)}$$

where RSS represents the range score signal (as calculated in Eq.4 or Eq.6).

In procedure 166, a range estimate is calculated using the maximum value index range bin (index of maximum range). Referring to FIG. 1, processor 114 calculates a range estimate of the target by multiplying the maximum value index range bin with the range bin spacing, as follows:

$$trg\_rng = rng\_bin * dr \qquad \text{(Eq. 8)}$$

where: "rng_bin" represents the maximum value index range bin (as calculated in Eq.7), and "dr" represents the range bin spacing or separation of the range spectrum RSS.

Figure 4A:
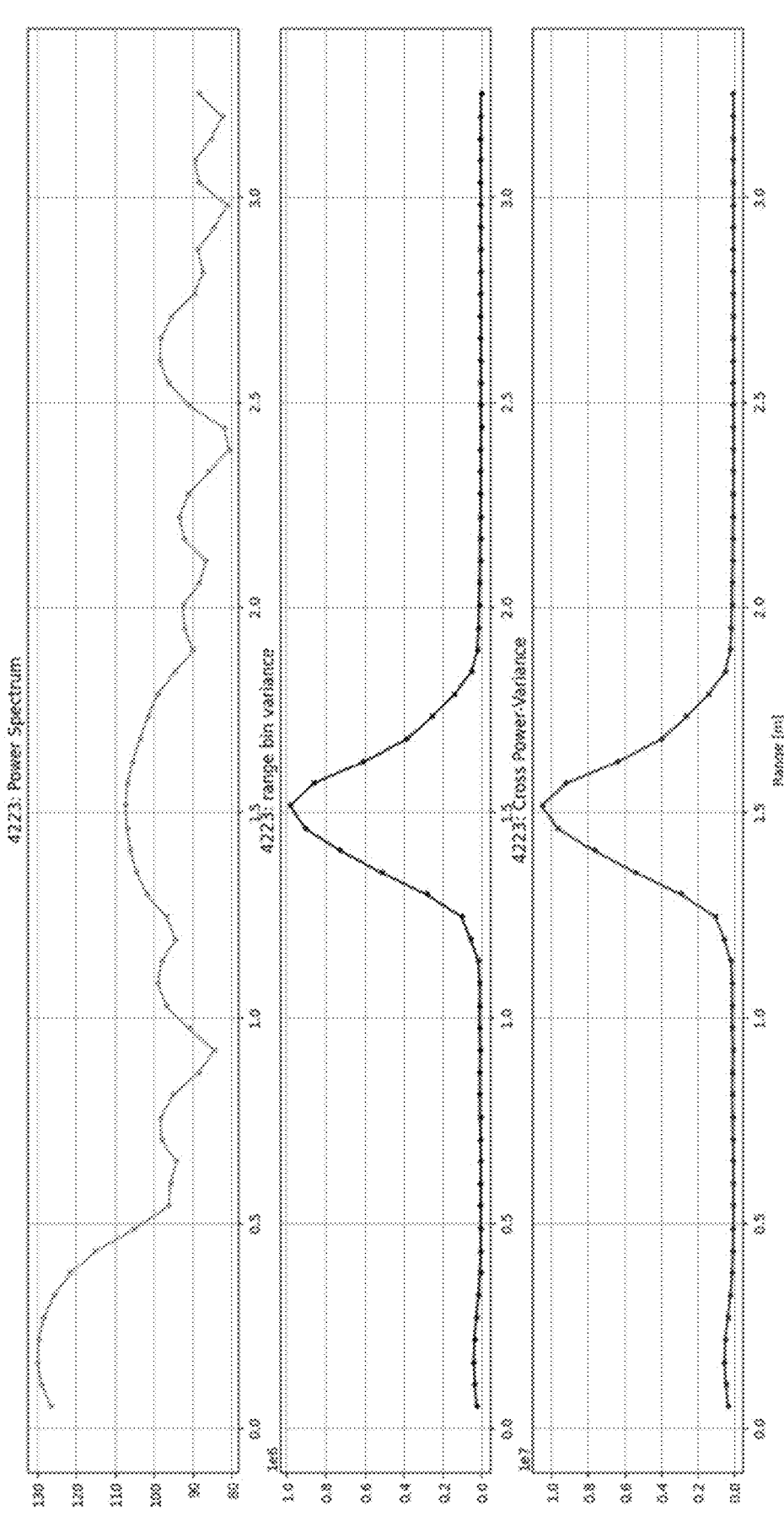
FIGS. 4A-4F are illustrations of spectral functions of mean power, range variance, and range score signal (RSS), for exemplary range determination test cases under different scenarios, operative in accordance with embodiments of the present invention.
Figure 4B:
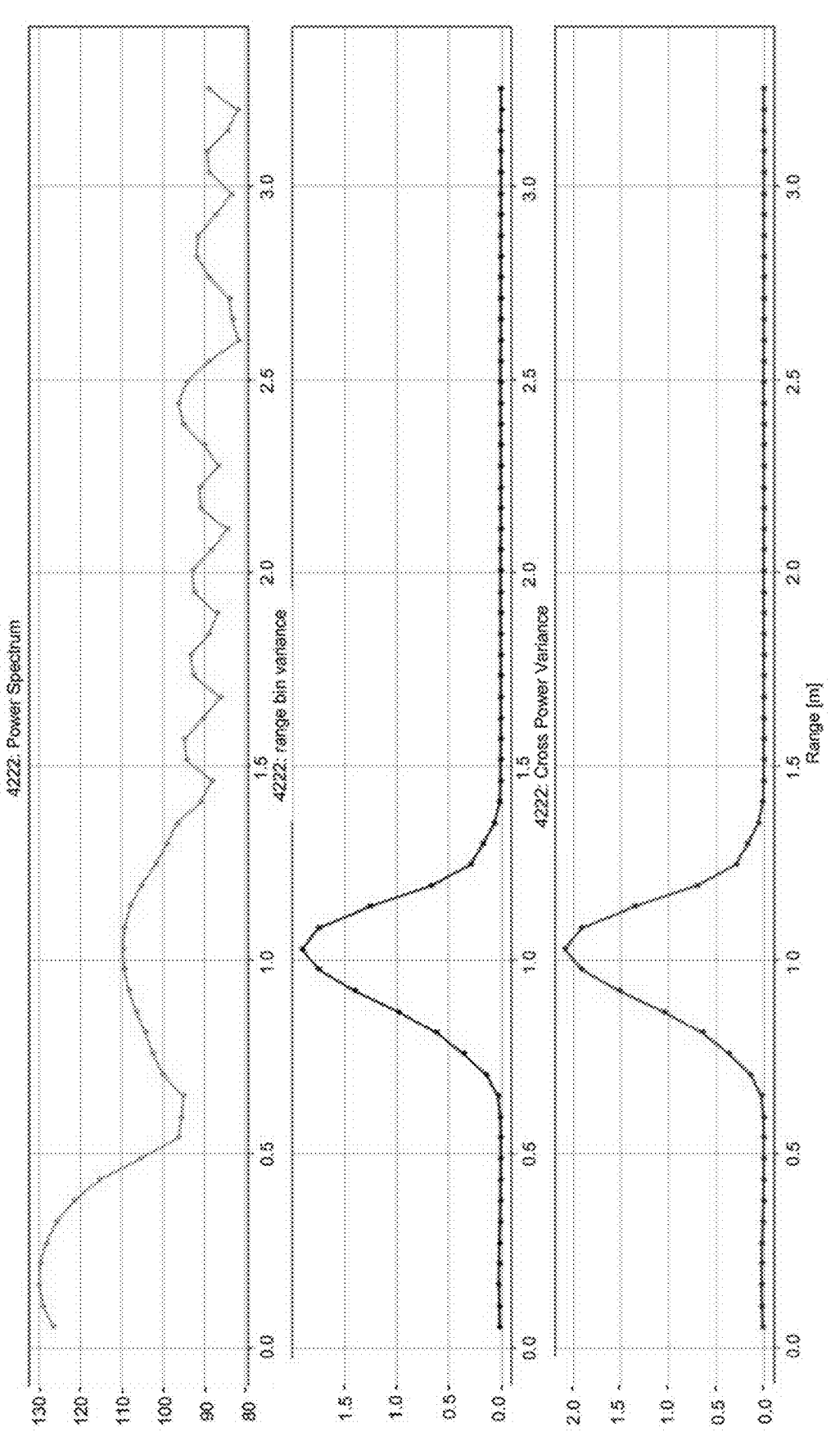
Figure 4C:
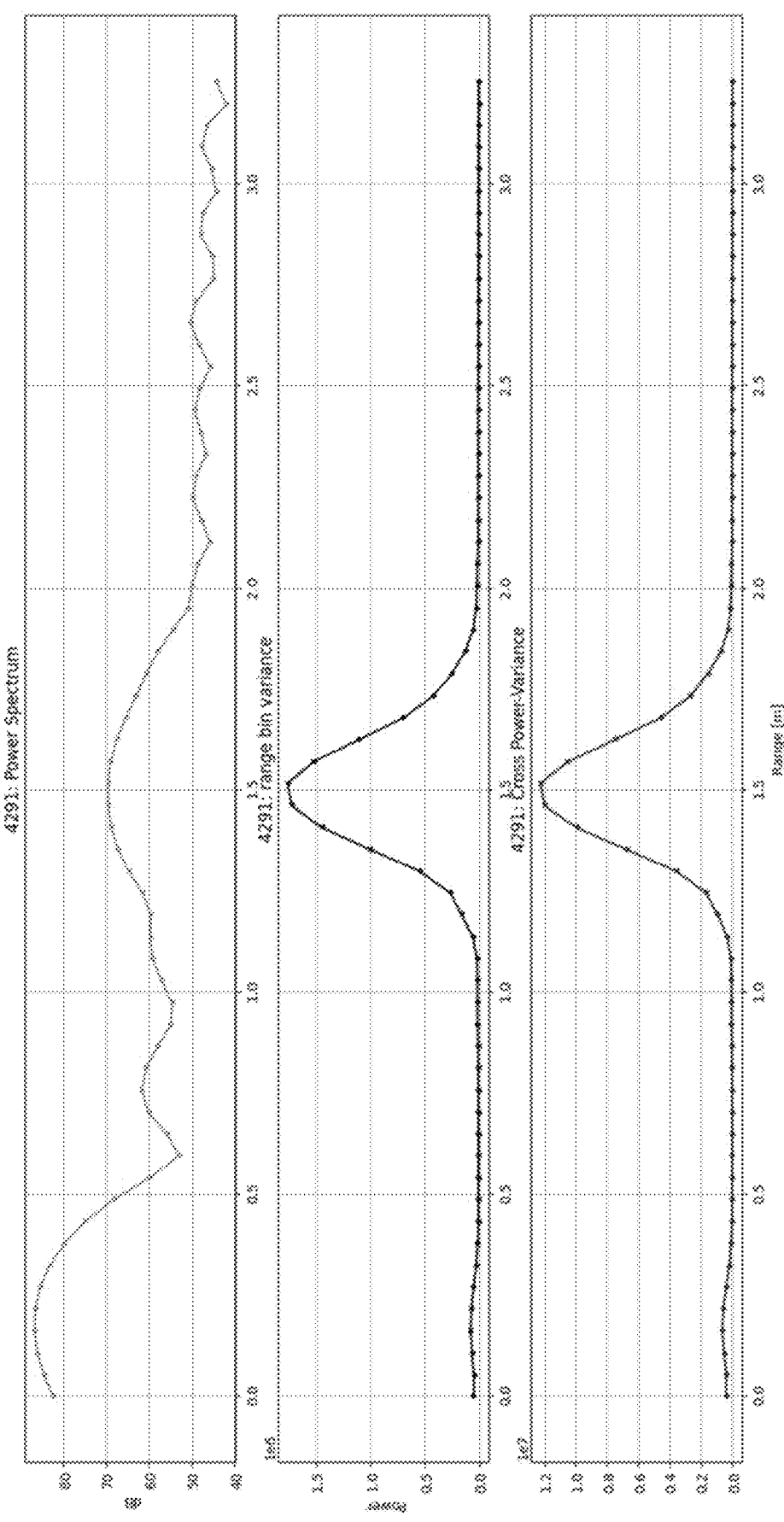
Figure 4D:
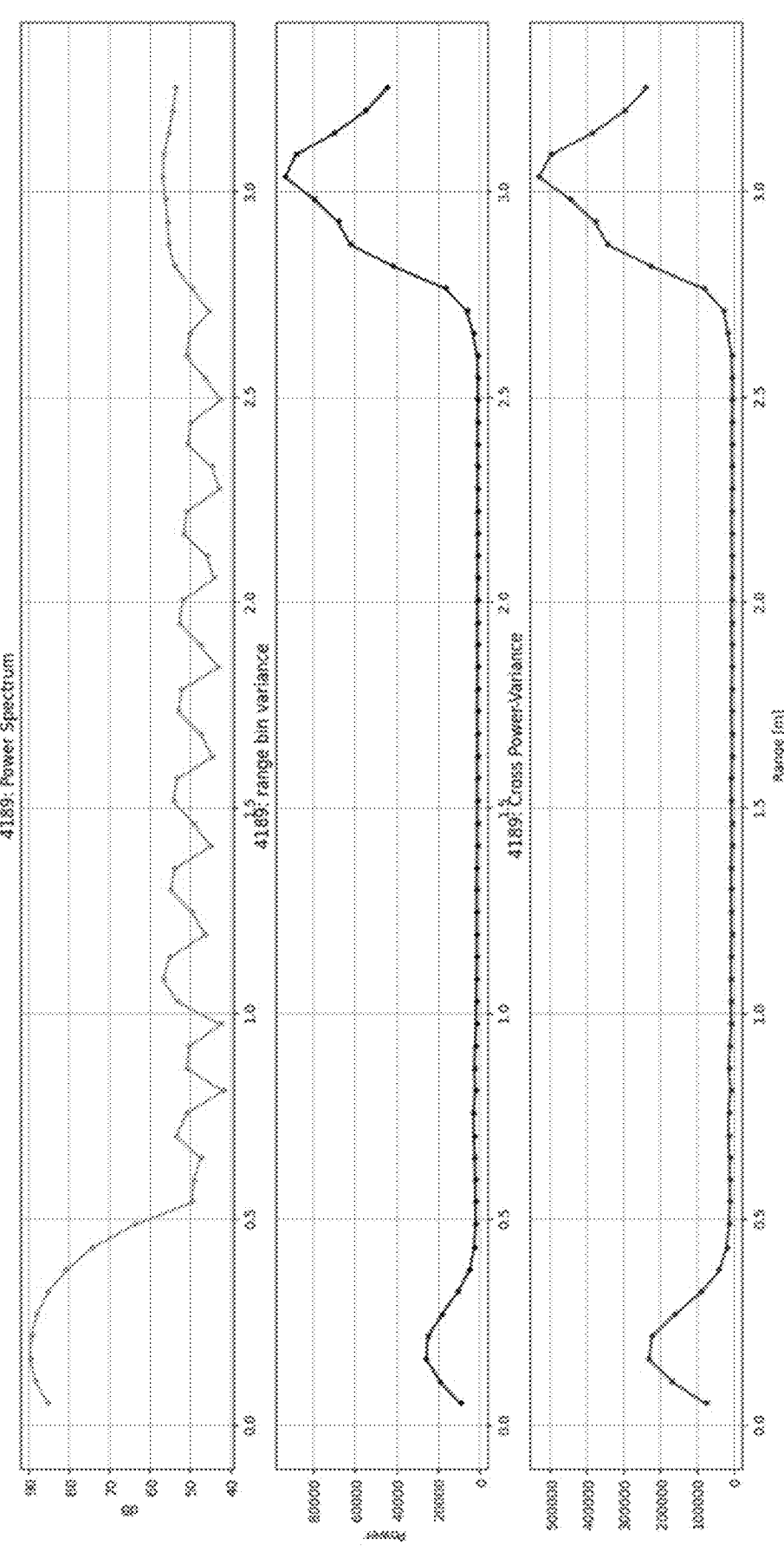
Figure 4E:
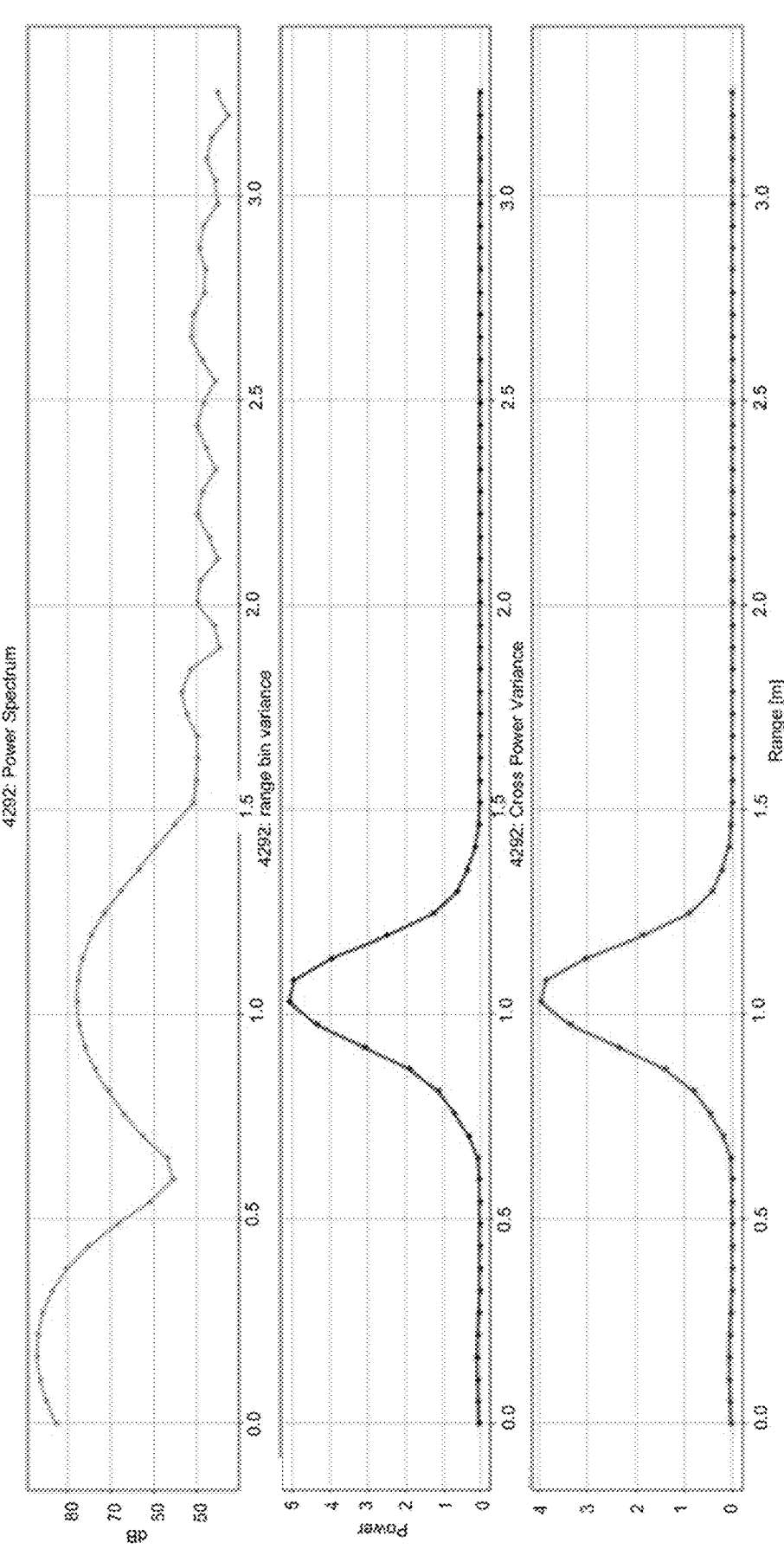
Figure 4F:
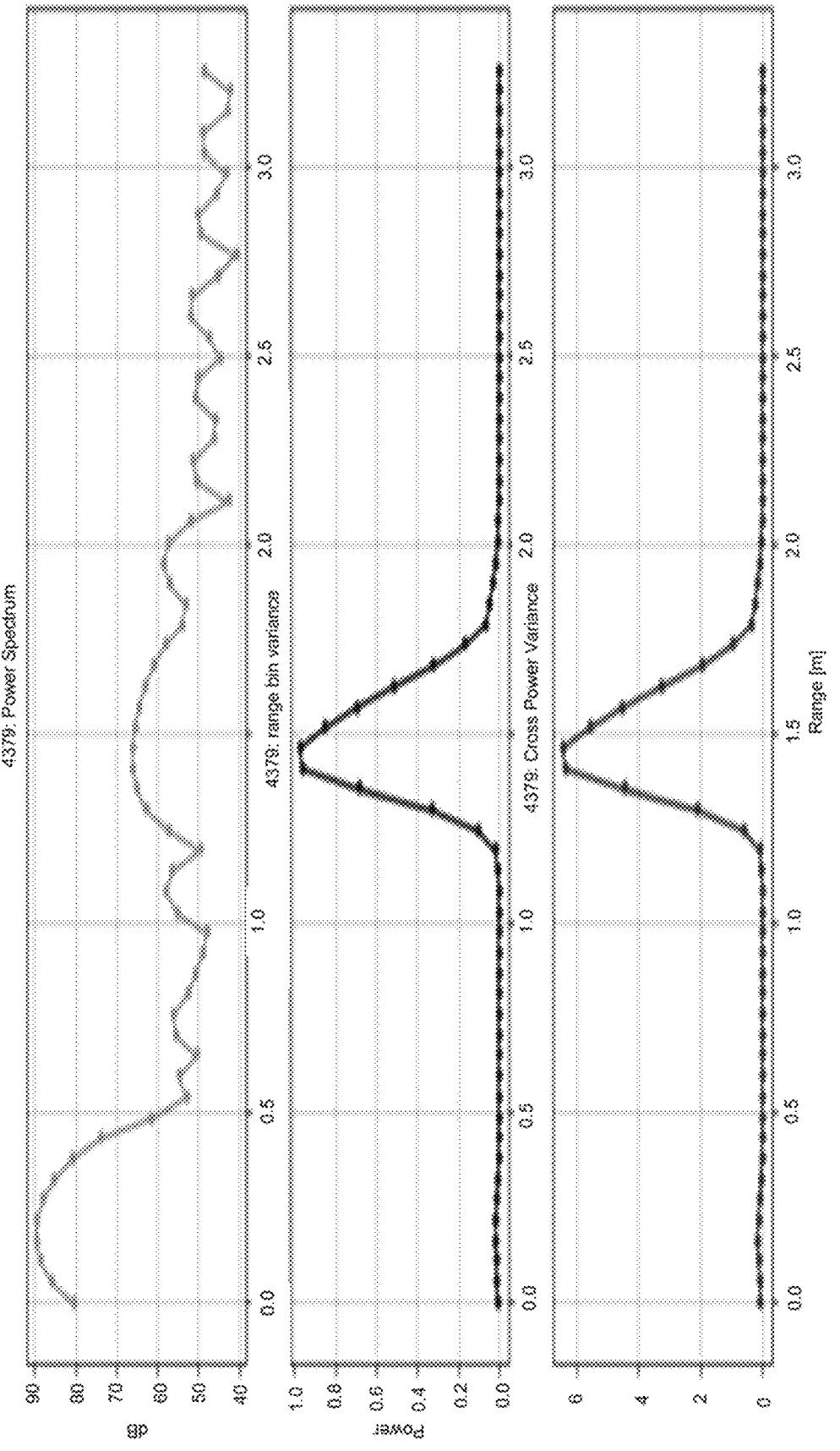

Reference is made to FIGS. 4A-4F, which illustrate spectral functions of mean power, range variance, and range score signal (RSS) (denoted as "cross-range variance"), for exemplary range determination test cases under different scenarios. FIG. 4A depicts power, range variance and RSS functions for a test case in which a subject is sitting at a measured distance of 1.50 meters (m) and the calculated range estimate is 1.52 m (e.g., where the measured distance between the subject and radar detector is measured manually, such as using a tape measure). FIG. 4B depicts a test case where the subject is sitting at a measured distance of 1.00 m and the calculated range estimate is 1.03 m. FIG. 4C depicts a test case where the subject is standing in an open space (i.e., located in the middle of a room and not adjacent to a supporting surface such as a wall, a chair or a bed) at a measured distance of 1.50 m and the calculated range estimate is 1.52 m. FIG. 4D depicts a test case where the subject is leaning on a wall at a measured distance of 3.00 m and the calculated range estimate is 3.03 m. FIG. 4E depicts a test case where the subject is lying down on a bed at a measured distance of 1.00 m and the calculated range estimate is 1.03 m. FIG. 4F depicts a test case where the subject is sitting down with a zero respiration rate (e.g., holding his breath) at a measured distance of 1.50 m and the calculated range estimate is 1.53 m.

Referring back to FIG. 3, the calculated range estimate is validated in an optional "validation" stage 170, which includes procedures 171, 172, 173, 174. Validation metrics are established to provide an indication of whether the range estimate of the target is indeed valid. Four different validation metrics are defined. One validation metric is based on a modified z-score, another is based on an inter-quartile range (IQR) outlier value, a third metric is based on a maximum/minimum ratio of a range detection metric, and a fourth metric is based on a number of positive peaks in a modified z-score signal.

In procedure 171, a first validity metric of the calculated range estimate is determined. Referring to FIG. 1, processor 114 determines a first validity metric based on a max/min ratio ("mxmn"), such as by using the following equation:

$$mxmn = max(RSS)/min(RSS) \qquad \text{(Eq. 9)}$$

where RSS represents the range score signal (as calculated in Eq.4 or Eq.6).

Processor 114 then determines whether the calculated range estimate meets a first validation criterion by examining whether the calculated max/min ratio exceeds a predetermined threshold value, which can be modified to reflect different levels of sensitivity. For example, the threshold value may be set to 100, as follows:

$$valid_1 = positive \text{ if } mxmn > 100 \qquad \text{(Eq. 10)}$$

In procedure 172, a second validity metric of the calculated range estimate is determined. Referring to FIG. 1, processor 114 determines a second validity metric based on an inter-quartile range (IQR) metric outlier ("trg_igr"), by using the following formula:

i) calculate the lower quartile ($q_{0.25}$) and upper quartile ($q_{0.75}$) values;

ii) calculate the different between the lower quartile ($q_{0.25}$) and the upper quartile ($q_{0.75}$) to obtain the IQR or mid-spread;

iii) multiple the IQR by 1.5 to obtain the IQR-outlier threshold.

This formula can be expressed as follows:

$$\text{iqr\_outlier} = (q_{0.25} - q_{0.75}) * 1.5 \qquad \text{(Eq. 11)}$$

Processor 114 then determines whether the calculated range estimate meets a second validation criterion by examining whether the maximum RSS value exceeds the calculated IQR-outlier value, as follows:

$$\text{valid}_2 = \text{positive if } \max(RSS) > \text{iqr\_outlier} \qquad \text{(Eq. 12)}$$

Figure 6:
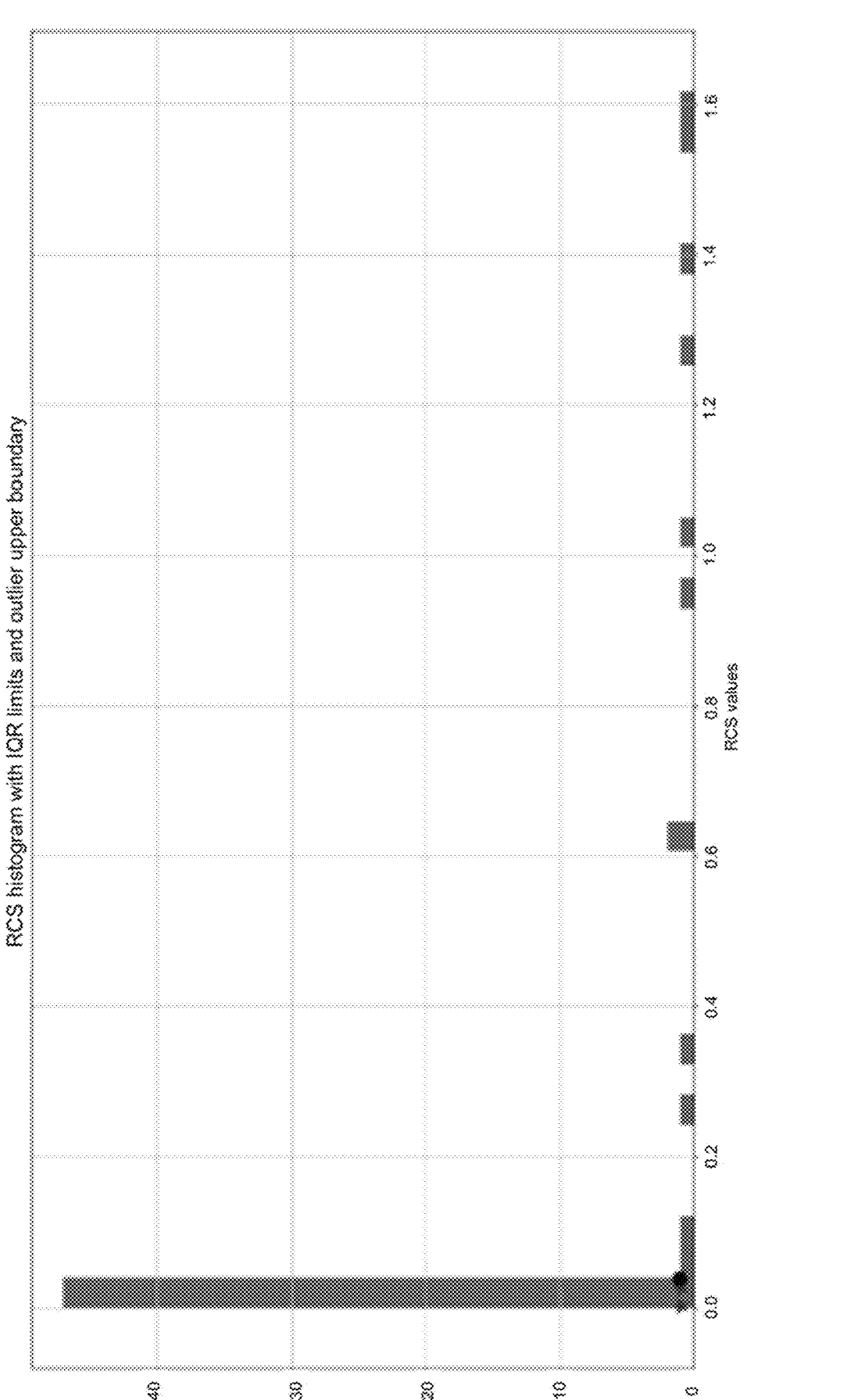
FIG. 6 is an illustration of a range score signal (RSS) histogram with IQR limits for an exemplary range determination test case, operative in accordance with an embodiment of the present invention.

Reference is made to FIG. 6, which illustrates a range score signal (RSS) histogram with IQR limits for an exemplary range determination test case. The red stars signify the IRQ boundary of the central 50% data. The black diamond signifies the outlier boundary. All of the values above a threshold are considered "outliers" according to a normal distribution. A target range bin having an extremely high value with respect to the surrounding range bins is thus deemed an outlier for these purposes. It can be seen that the detected signal for this test case is indeed above the IQR outlier boundary (and therefore meets the second validity criterion).

In procedure 173, a third validity metric of the calculated range estimate is determined. Referring to FIG. 1, processor 114 determines a third validity metric based on a modified (biased) z-score metric, by using the following formula:

i) calculate a modified standardized z-score of the power signal as follows:

$$\textit{zscore} = (RSS - (\mu + k \cdot \sigma))/\sigma \qquad \text{(Eq. 13)}$$

where RSS represents the range score signal (as calculated in Eq.4 or Eq.6); "$\mu$" represents the mean of the RSS; "$\sigma$" represents the standard deviation of the RSS; and "k" is a positive integer accounting for a level of thresholding of the main target peak (i.e., defining how dominant the target peaks are relative to the rest of the range signal by adding a bias ($k \cdot \sigma$) to $\mu$).

ii) apply the sign operator:

$$\text{sign\_zc} = \text{sign}(\textit{zscore}) \qquad \text{(Eq. 14)}$$

iii) append "−1" at the beginning and end of the resultant vector to address edge detection cases;

iv) apply a differential (diff) operator followed by an absolute (abs) operator to obtain "diff_sign_zc":

$$\text{diff\_sign\_zc} = \text{abs}(\textit{diff}(\text{sign\_zc})) \qquad \text{(Eq. 15)}$$

v) find indices where:

$$\text{zc\_idx} = \text{diff\_sign\_zc} > 0. \qquad \text{(Eq. 16)}$$

Processor 114 then determines whether the calculated range estimate meets a third validation criterion by examining if the following 2 conditions are met:

valid$_3$=positive if:

$$a. \text{ length(zc\_idx)} = 2; \text{ and} \qquad \text{(Eq. 17)}$$

$$b. \text{ zc\_idx[0]} < \text{rng\_bin} < \text{zc\_idx[1]}. \qquad \text{(Eq. 18)}$$

Figure 5A:
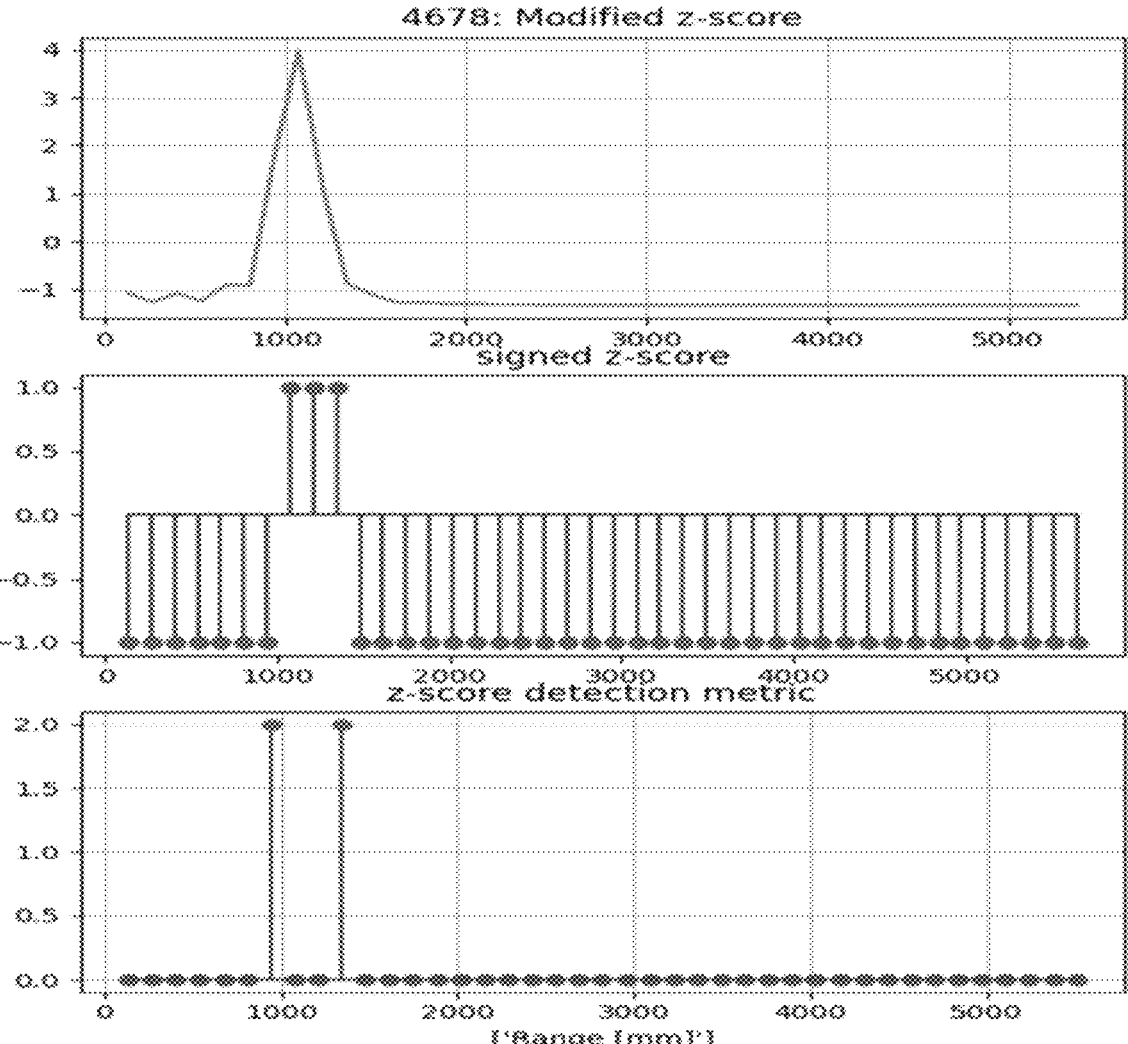
FIGS. 5A-5B are illustrations of modified z-score functions for exemplary range determination test cases under different scenarios, operative in accordance with embodiments of the present invention.
Figure 5B:
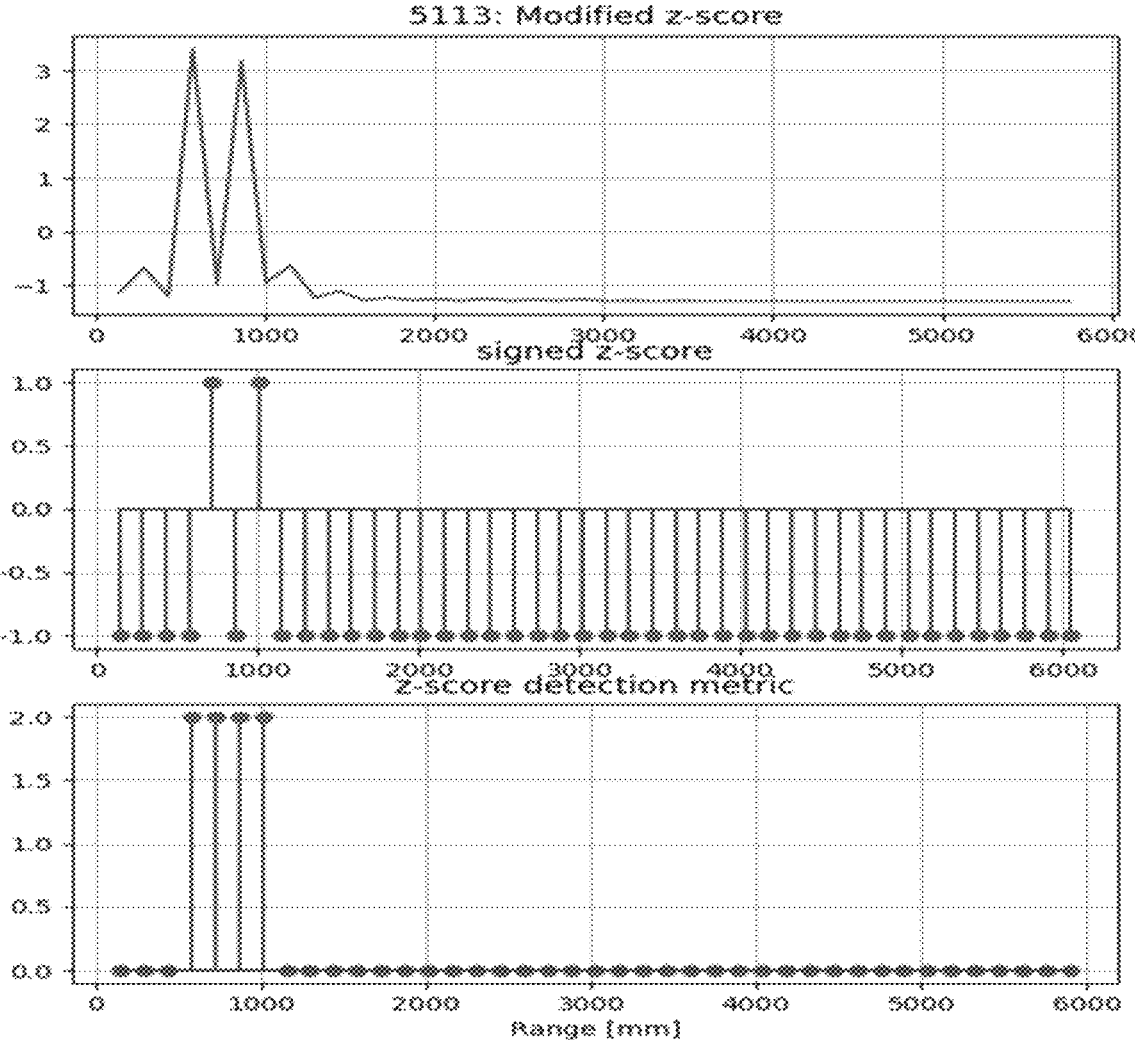

Reference is made to FIGS. 5A-5B, which illustrate modified z-score functions for exemplary range determination test cases under different scenarios. It can be seen that in the example of FIG. 5A the modified z-score function is "valid" (i.e., the third validity criterion is met, since length (zc_idx)=2), whereas in the example of FIG. 5B the modified z-score function is "invalid" (i.e., the third validity criterion is not met since length(zc_idx)=4).

In procedure 174, a fourth validity metric of the calculated range estimate is determined. Referring to FIG. 1, processor 114 determines a fourth validity criterion based on the number of z-score signal peaks. Processor 114 determines whether the calculated range estimate meets a fourth validation criterion by examining whether the number of z-score signal peaks is equal to 1:

$$\text{valid}_4 = \text{positive if n\_peaks} == 1. \qquad \text{(Eq. 19)}$$

Figure 7A:
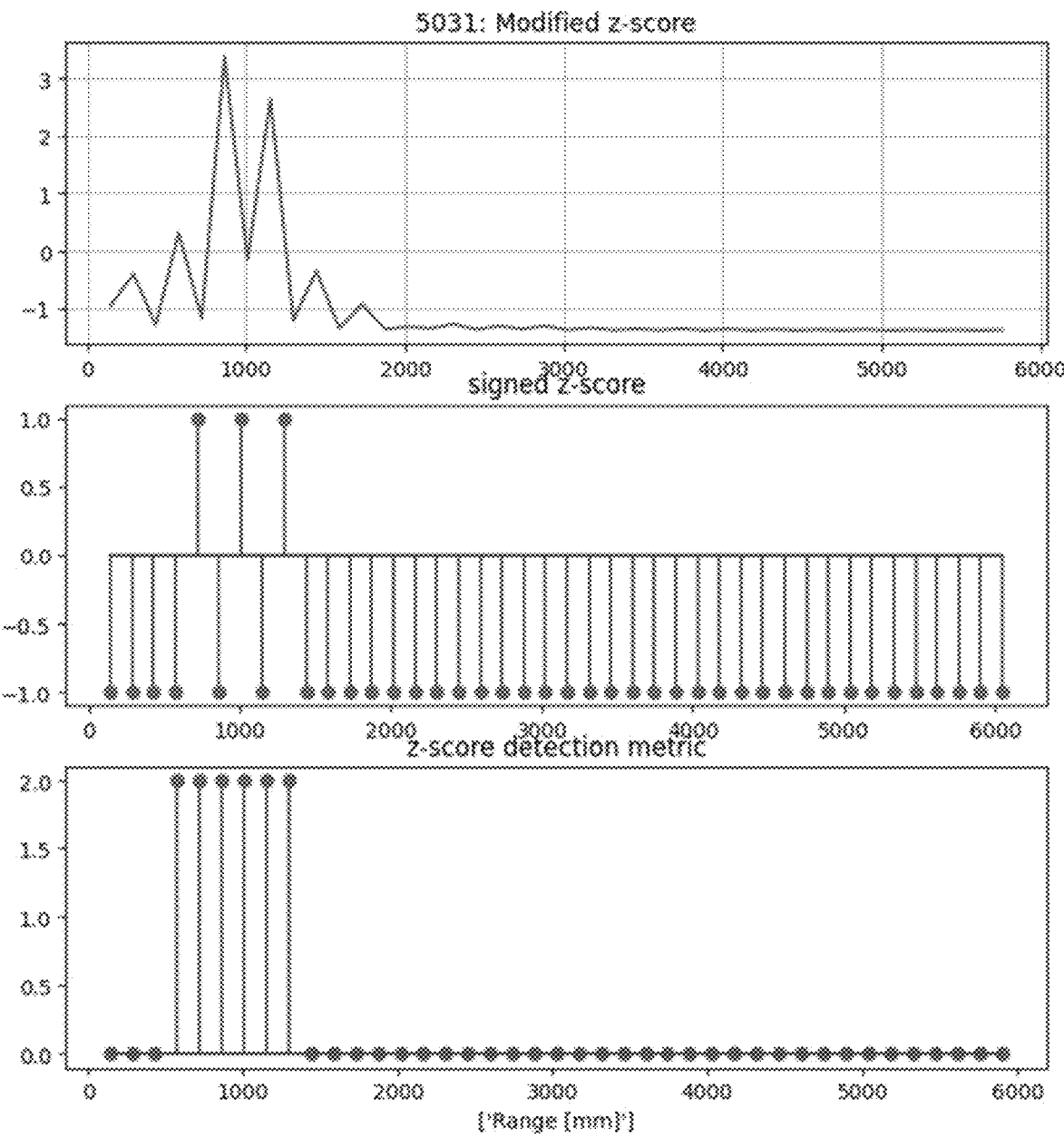
FIGS. 7A-7B are illustrations of modified z-score functions for exemplary range determination test cases under different scenarios, operative in accordance with embodiments of the present invention.
Figure 7B:
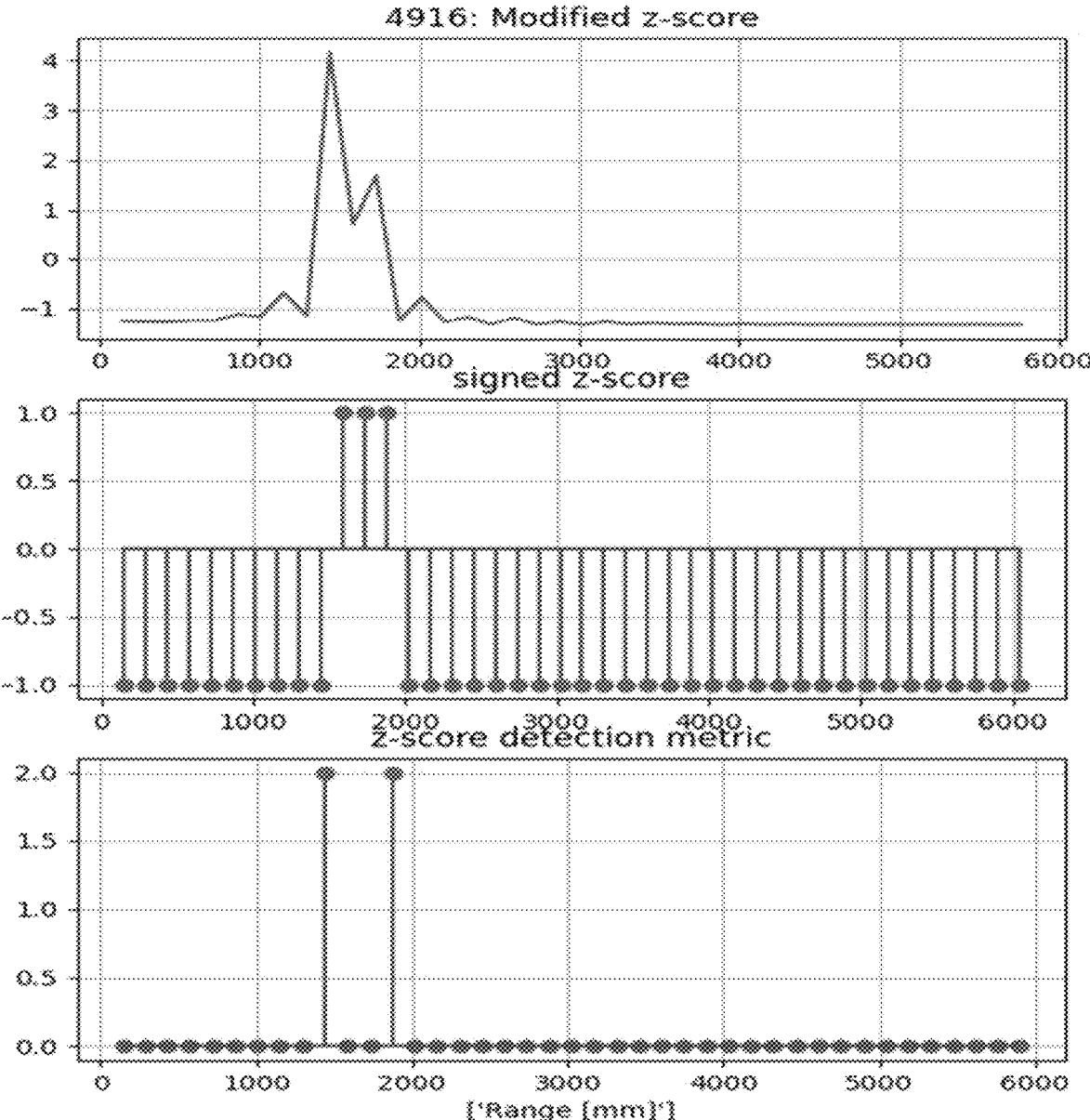

Reference is made to FIGS. 7A and 7B, which illustrate modified z-score functions for exemplary range determination test cases under different scenarios. Both of the cases depicted in FIGS. 7A and 7B represent invalid range estimate where the modified z-score signal has two peaks. However, the modified z-score is identified as invalid (i.e., does not pass the third validity criterion) in FIG. 7A, but is validated (i.e., meets the third validity criterion) in the case of FIG. 7B since the dip between the two z-score peaks has a positive value. Therefore, the fourth validity criterion assists in properly invalidating the signal despite the positive third validity result in FIG. 7B, as the number of z-score peaks is deemed invalid (i.e., fails to meet the fourth validity criterion) for both cases.

After each of the four validity criteria is determined, processor 114 applies a global validation based on the number of positively validated criteria. In particular, if at least a selected number (N) of validity criteria are affirmed (i.e., if at least N criteria are positive), then the range estimate candidate (determined in procedure 166) is validated, whereas if less than the selected number (N) of validity criteria are affirmed (i.e., if less then N criteria are positive) then the range estimate candidate is deemed invalid. For example, the selected number of validation criteria may be four (4), such that the range estimate candidate is validated only when all four validation metrics are affirmed (i.e., all of the validation criteria are met), but is not validated if three or fewer validity metrics are affirmed. If the range estimate candidate is deemed to be "invalid", a predefined default range value may be established instead, and a new reflected radar signal may be sampled and processed. If the range estimate candidate is deemed to be "valid", then the range estimate is established as a final range determination in procedure 180. If the range estimate is valid then no further estimate may be obtained until a new session is initialized. In general, an obtained range estimate may be utilized or discarded according to its validation results in accordance with suitable rules, which may be predefined or may be established or updated by an operator of system 110.

Figure 8A:
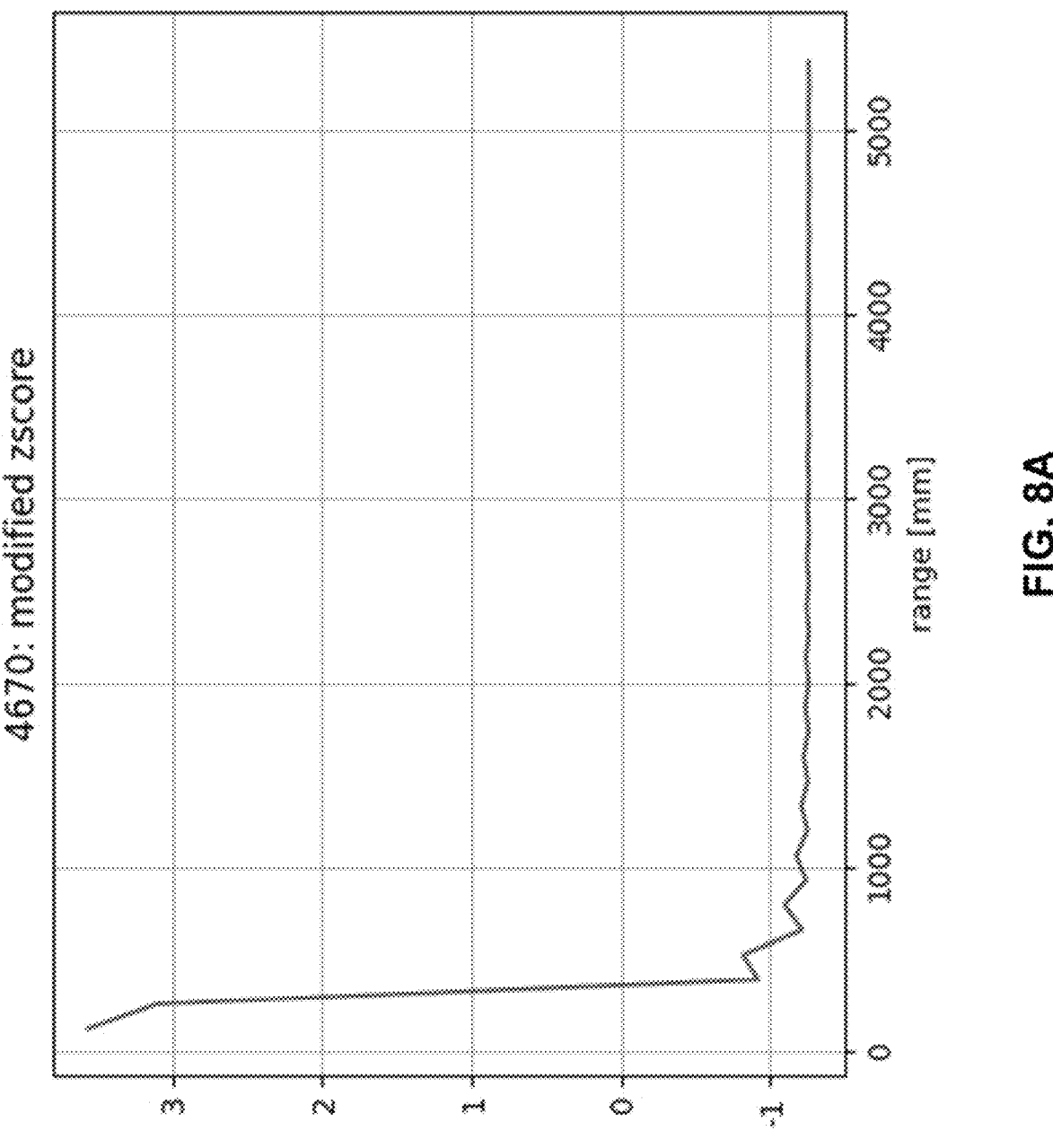
FIGS. 8A-8B are illustrations of modified z-score functions for exemplary range determination test cases under different scenarios, operative in accordance with embodiments of the present invention.
Figure 8B:
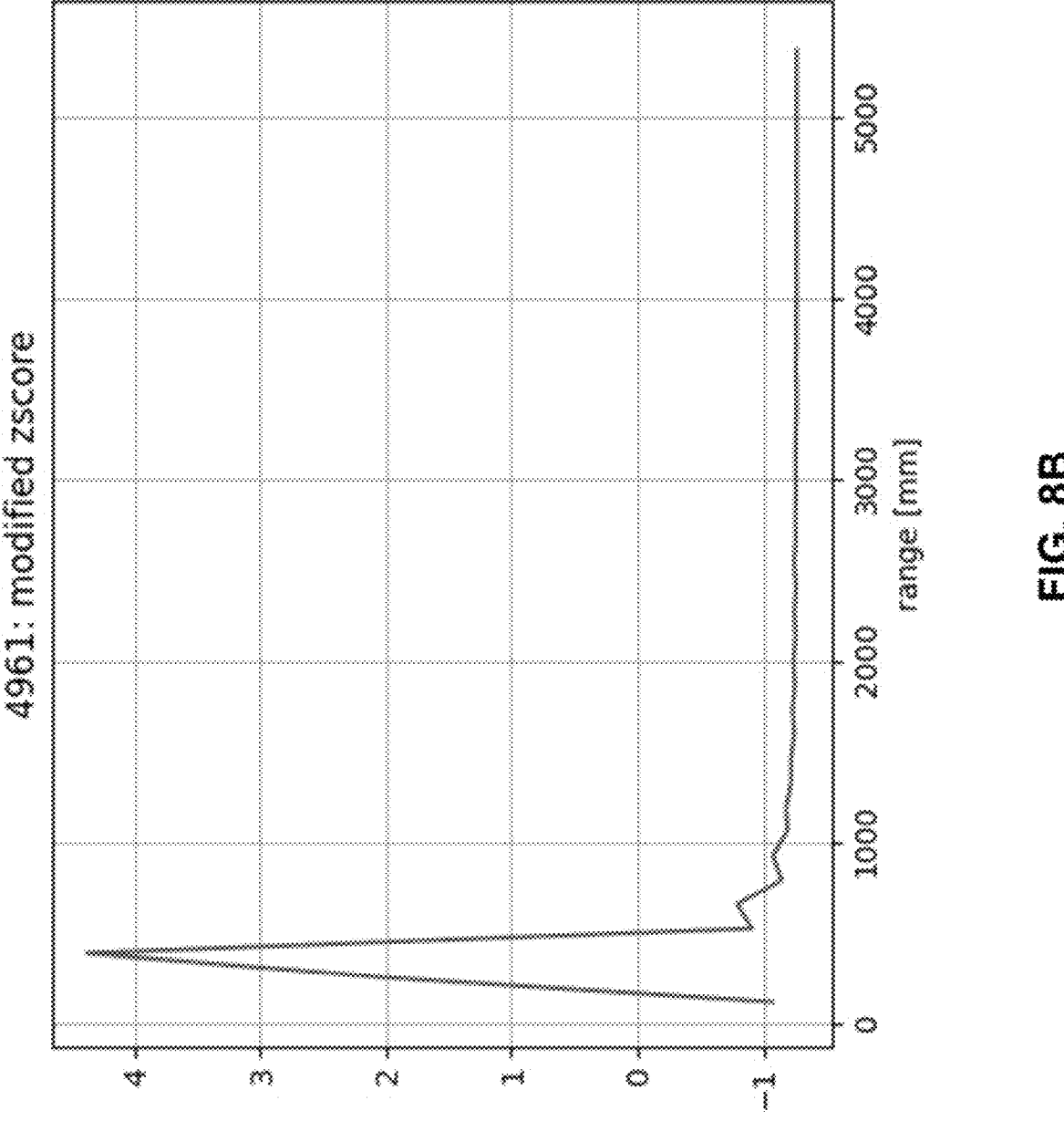

An auxiliary criterion may be applied in certain scenarios resulting in the obtained range estimate being discarded and replaced by a default range value. One example may be when the subject 120 is positioned in a sitting or lying down posture (i.e., a non-standing posture) and facing away from radar detector 112, such that the reflected radar signal is obtained from the back of subject 120. Another example is if the range estimate is smaller than a predefined minimum threshold range (e.g., 30 cm), which may be established or updated by a system operator. In such cases, the range estimate may be overridden or deemed invalid, and a default range estimate may be utilized instead. However, a range estimate may be obtained using the disclosed method for any non-zero ranges. Reference is made to FIGS. 8A and 8B, which illustrate modified z-score functions for exemplary range determination test cases under different scenarios. In both FIGS. 8A and 8B, the range estimates are obtained from the back (i.e., the subject is facing away from the radar detector) at a distance of approximately 100 millimeters (mm).

In procedure 150, one or more physiological parameters of the subject is detected. Referring to FIG. 1, processor 114 processes reflected radar signal 122 received by range detector 112 to obtain one or more physiological parameters or vital signs of subject 120, such as a heartbeat, pulse, respiration rate, or body movements. Processor 114 may verify that the subject is a living entity (rather than an inanimate object) when valid physiological parameters are extracted from reflected signal 122, as these physiological parameters effectively manifest variance in the RTM range bins resulting from movement of the subject. If valid physiological parameters or vital signs cannot be extracted from reflected signal 122, then the signal may be determined to have been reflected from a non-living entity or an inanimate stationary object, such as a wall or chair. Accordingly, the coupling of the range estimation via the propagation delay of the radar signal and the range variance resulting from physiological parameters of the subject, effectively allows for the subject range measurement utilizing radar, in contrast to an inanimate stationary object which will have no variance in its location (at least during the observation period when obtaining the radar signal). In addition, the range estimate may provide dynamic feedback for calibrating or focusing reception of the reflected radar signal to enable the physiological parameters detection. Since the subject position may shift dynamically, such as due to forward or backward movement of subject 120 relative to radar detector 112, the range estimate (obtained in procedure 160) may provide a correct position for radar detector 112 to focus on in order to ensure that the received radar signal 122 was reflected from subject 120 and not from nearby objects, such that psychological parameters of subject 120 can be properly extracted from the received reflected radar signal 122.

Figure 9:
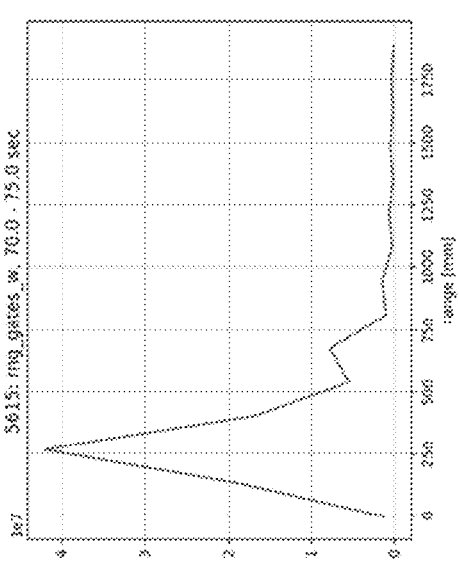
FIG. 9 is an illustration of an exemplary range bin spectral function transitioning over time due to movement of a sitting subject, operative in accordance with an embodiment of the present invention.
Figure 9:
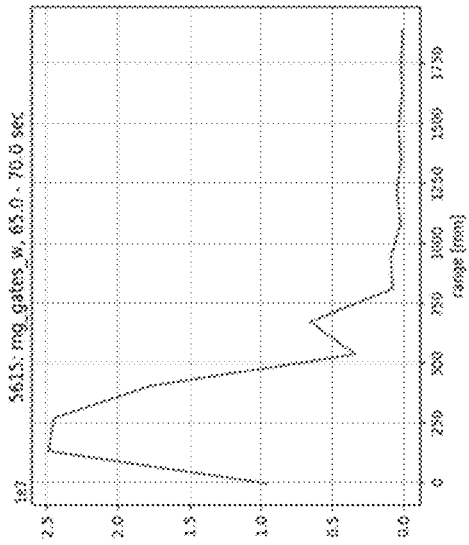
Figure 9:
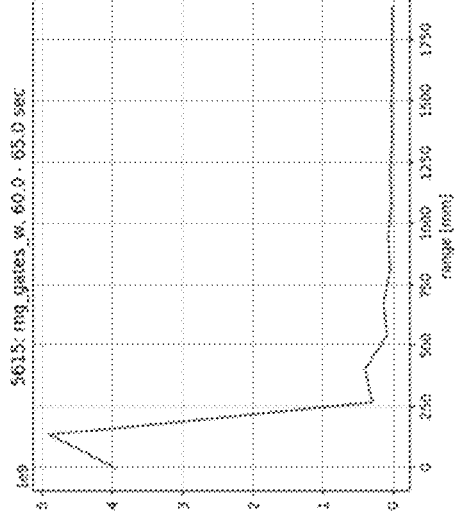

Reference is made to FIG. 9, which illustrates an exemplary range bin spectral function transitioning over time due to movement of a sitting subject. FIG. 9 depicts the migration of the identified range bins (in procedure 165) due to movement of a sitting subject in a sitting posture. The range migration of the position of the subject is detected over time of session due to the translocation or displacement of the subject, showing how the physiological parameters can project variance in the subject movement.

The method of FIGS. 2 and 3 is generally implemented in an iterative manner, such that at least some of the procedures are performed repeatedly, in order to provide a dynamic range determination and validation in real-time.

The disclosed system and method may also be used to provide a three-dimensional (3D) locational measurement of the subject by providing an angle measurement, such as via standard angle of arrival (AOA) estimation techniques known in the art. Accordingly, the angular measurement can provide two-dimensional position coordinates of the subject, which combined with the range measurement can provide a three-dimensional position measurement. For example, the angle measurement may include azimuth and elevation angles, utilizing a multiple-input multiple-output (MIMO) radar processing scheme, which mandates multiple antennas on the radar device (e.g., a minimum of one transmitting antenna (Tx) and two receiving antennas (Rx), or a minimum of two transmitting antenna (Tx) and one receiving antenna (Rx), or any larger number combination thereof).

It is noted that system 110 operates remotely and does not require direct physical contact with subject 120. In particular, radar detector 112 obtains reflected radar signal 122 remotely, without requiring any components being in direct physical contact with subject 120 or being worn or attached to subject 120. It is further noted that radar signal 122 may be obtained from any direction of subject 120, such as from in front or behind or from an angle relative to subject 120 (i.e., in relation to the position and orientation of radar detector 112). Furthermore, radar signal 112 may be obtained in low light or poor visibility conditions. The disclosed system does not require costly equipment and has relatively few components, and is relatively straightforward to operate and maintain.

The disclosed range estimation and validation method can be used for various applications. For example, the disclosed method can be used to detect different movements or positions of a subject in different postures, such as sitting, standing, or laying down, such as detecting whether the subject is leaning in a certain direction (forward, backward or to the side) when sitting on a chair or when laying down on a bed. The obtained range estimate may serve to provide a calibrated range immediately before or immediately after a change in posture by the subject, such as in order to calibrate reception of the reflected radar signal from the subject to enable detection of vital signs or psychological parameters of the subject. The disclosed method can also be used for monitoring patients in vulnerable situations, such as to detect an eldercare subject who may be falling off a bed or sleeping with his/her head in a precarious position, or to detect infants or young children left inadvertently in a parked vehicle. Accordingly, the radar detector and/or other components of the disclosed system may be mounted above or beneath or adjacent to a furniture item used by a monitored subject, such as: a bed, a chair, a sofa, a vehicle seat, and the like.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

The invention claimed is:

1. A method for determining the range of a subject, the method comprising:

receiving a frequency-modulated continuous-wave (FMCW) radar signal reflected from at least one subject;

sampling the received reflected radar signal to generate a plurality of sample vectors over a selected duration, each sample vector comprising a plurality of signal samples for each frame of the reflected radar signal;

applying a fast Fourier transform (FFT) to a plurality of sample vectors over a selected duration to generate a range-time map (RTM) data matrix;

determining an initial range estimate of the subject by:

(i) calculating a range score signal (RSS) using an equation selected from the group consisting of: a) cross-multiplying a mean power per range bin of the RTM with a corresponding variance per range bin (RSS=Mean Power×rng_var); and b) dividing the variance per range bin of the RTM with a zero-crossing per range bin to the second exponent $$\left(RSS = \frac{rng\_var}{ZC^2}\right);$$

(ii) identifying a maximum value index range bin having a maximum RSS value; and (iii) calculating a range estimate by multiplying the identified maximum value index range bin with a range bin spacing of the range spectrum RSS;

validating the determined range estimate by:

determining if the range estimate meets a first validity criterion based on a max/min dynamic ratio (mxmn);

determining if the range estimate meets a second validity criterion based on an inter-quartile range (IQR) outlier metric;

determining if the range estimate meets a third validity criterion based on a modified z-score; and determining if the range estimate meets a fourth validity criterion based on the number of signal peaks of the standardized z-score;

establishing a final range of the subject according to the range estimate if the range estimate is determined to meet at least a predetermined number of the validity criteria; and detecting at least one physiological parameter of the subject to verify that the subject is a living entity.

2. The method of claim 1, wherein determining if the range estimate meets a first validity criterion comprises:

calculating a max/min dynamic ratio (mxmn) value according to the formula: mxmn=max(RSS)/min (RSS); and checking if the calculated max/min dynamic ratio (mxmn) exceeds a predetermined threshold value: $valid_1$=positive if mxmn>V.

3. The method of claim 1, wherein determining if the range estimate meets a second validity criterion comprises:

calculating a lower quartile value ($q_{0.25}$) and an upper quartile value ($q_{0.75}$);

calculating an inter-quartile range (IQR) value based on a difference between the lower quartile value ($q_{0.25}$) and the upper quartile value ($q_{0.75}$);

calculating an inter-quartile range outlier (IQR-outlier) value by multiplying the IQR value by a factor of 1.5: iqr_outlier=($q_{0.25}$–$q_{0.75}$)*1.5; and checking if the calculated inter-quartile range outlier (IQR-outlier) value exceeds a maximum range score signal value: $valid_2$=positive if max(RSS)>iqr_outlier.

4. The method of claim 1, wherein determining if the range estimate meets a third validity criterion comprises:

calculating a modified z-score value according to the formula:

$$zscore = (RSS - (\mu + k \cdot \sigma))/\sigma;$$

applying a sign operator to the calculated modified z-score: sign_zc=sign(zscore);

appending −1 at beginning and end of resulting vector;

applying a difference operator followed by absolute operator on the result: diff_sign_zc=abs(diff(sign_zc));

identifying indices where zc_idx=diff_sign_zc>0; and checking if the following two conditions are met:

(i) length(zc_idx)=2; and (ii) zc_idx[0]<rng_bin<zc_idx[1].

5. The method of claim 1, wherein determining if the range estimate meets a fourth validity criterion comprises:

calculating a modified z-score value according to the formula:

$$zscore = (RSS - (\mu + k \cdot \sigma))/\sigma;$$

and checking if the number of signal peaks of the calculated z-score is equal to 1: $valid_4$=positive if n_peaks==1.

6. The method of claim 1, further comprising the procedure of zero-padding the sample vectors to extend vector length in accordance with a desired range accuracy.

7. The method of claim 1, wherein the determined range estimate is replaced with a default range value if at least one auxiliary criterion is met, the auxiliary criterion selected from the group consisting of:

the subject is positioned in a non-standing posture and the reflected radar signal is received from back of the subject; and the determined range estimate is below a predefined minimum threshold range.

8. A system for determining the range of a subject, the system comprising:

a radar detector, configured to receive a frequency-modulated continuous-wave (FMCW) radar signal reflected from at least one subject, and to sample the received reflected radar signal to generate a plurality of sample vectors over a selected duration, each sample vector comprising a plurality of signal samples for each frame of the reflected radar signal; and a processor, configured to:

apply a fast Fourier transform (FFT) to a plurality of sample vectors over a selected duration to generate a range-time map (RTM) data matrix, determine an initial range estimate of the subject by: (i) calculating a range score signal (RSS) using an equation selected from the group consisting of: a) cross-multiplying a mean power per range bin of the RTM and the corresponding variance per range bin (RSS=Mean Power×rng_var); and b) dividing the variance per range bin of the RTM with a zero-crossing per range bin to the second exponent $$\left(RSS = \frac{\text{rng\_var}}{ZC^2}\right);$$

(ii) identifying a maximum value index range bin having a maximum RSS value; and (iii) calculating a range estimate by multiplying the identified maximum value index range bin with a range bin spacing of the range spectrum RSS, validate the determined range estimate by: determining if the range estimate meets a first validity criterion based on a max/min dynamic ratio (mxmn); determining if the range estimate meets a second validity criterion based on an inter-quartile range (IQR) outlier metric; determining if the range estimate meets a third validity criterion based on a modified z-score; and determining if the range estimate meets a fourth validity criterion based on the number of signal peaks of the standardized z-score, establish a final range of the subject according to the range estimate if the range estimate is determined to meet at least a predetermined number of the validity criteria, and detect at least one physiological parameter of the subject to verify that the subject is a living entity.

9. The system of claim 8, wherein determining if the range estimate meets a first validity criterion comprises:

calculating a max/min dynamic ratio (mxmn) value according to the formula: mxmn=max(RSS)/min(RSS); and checking if the calculated max/min dynamic ratio (mxmn) exceeds a predetermined threshold value: $valid_1$=positive if mxmn>V.

10. The system of claim 8, wherein determining if the range estimate meets a second validity criterion comprises:

calculating a lower quartile value ($q_{0.25}$) and an upper quartile value ($q_{0.75}$);

calculating an inter-quartile range (IQR) value based on a difference between the lower quartile value ($q_{0.25}$) and the upper quartile value ($q_{0.75}$);

calculating an inter-quartile range outlier (IQR-outlier) value by multiplying the IQR value by a factor of 1.5: iqr_outlier=($q_{0.25}-q_{0.75}$)*1.5; and checking if the calculated inter-quartile range outlier (IQR-outlier) value exceeds a maximum range score signal value: $valid_2$=positive if max(RSS)>iqr_outlier.

11. The system of claim 8, wherein determining if the range estimate meets a third validity criterion comprises:

calculating a modified z-score value according to the formula:

$$zscore = (RSS - (\mu + K \cdot \sigma))/\sigma;$$

applying a sign operator to the calculated modified z-score: sign_zc=sign(zscore);

appending −1 at beginning and end of resulting vector;

applying a difference operator followed by absolute operator on the result: diff_sign_zc=abs(diff(sign_zc));

identifying indices where zc_idx=diff_sign_zc>0; and checking if the following two conditions are met:

(iii) length(zc_idx)=2; and (iv) zc_idx[0]<rng_bin<zc_idx[1].

12. The system of claim 8, wherein determining if the range estimate meets a fourth validity criterion comprises:

calculating a modified z-score value according to the formula:

$$zscore = (RSS - (\mu + K \cdot \sigma))/\sigma; \text{ and}$$

checking if the number of signal peaks of the calculated z-score is equal to 1: $valid_4$=positive if n_peaks==1.

13. The system of claim 8, wherein the determined range estimate is replaced with a default range value if at least one auxiliary criterion is met, the auxiliary criterion selected from the group consisting of:

the subject is positioned in a non-standing posture and the reflected radar signal is received from back of the subject; and the determined range estimate is below a predefined minimum threshold range.

* * * * *